United States Patent
Kol et al.

(10) Patent No.: US 6,596,827 B2
(45) Date of Patent: Jul. 22, 2003

(54) METHOD FOR CATALYTIC POLYMERIZATION OF ALPHA-OLEFIN MONOMERS USING AN ULTRA-HIGH ACTIVITY NON-METALLOCENE PRE-CATALYST

(75) Inventors: Moshe Kol, Ramat Gan (IL); Edit Y. Tshuva, Rehovot (IL); Zeev Goldschmidt, Petach-Tikva (IL)

(73) Assignees: Ramot at Tel Aviv University Ltd., Tel Aviv (IL); Bar Ilanresearch and Development Company Ltd., Ramat Gan (IL)

( * ) Notice: Subject to any disclaimer, the term of this patent is extended or adjusted under 35 U.S.C. 154(b) by 35 days.

(21) Appl. No.: 09/903,660

(22) Filed: Jul. 13, 2001

(65) Prior Publication Data

US 2002/0019503 A1 Feb. 14, 2002

Related U.S. Application Data

(63) Continuation-in-part of application No. 09/394,280, filed on Sep. 10, 1999, now Pat. No. 6,333,423.

(51) Int. Cl.[7] .............................. C08F 4/44; C08F 4/64; C08F 4/642; C08F 4/643
(52) U.S. Cl. ...................... 526/161; 526/134; 526/172; 502/117; 502/103; 502/150
(58) Field of Search ................................ 526/161, 172, 526/134

(56) References Cited

U.S. PATENT DOCUMENTS 6,232,421 B1 * 5/2001 Fujita et al. ............. 526/348.6
6,333,389 B2 * 12/2001 Whiteker et al. ........... 526/161

* cited by examiner

Primary Examiner—David W. Wu
Assistant Examiner—R. Rabago
(74) Attorney, Agent, or Firm—G. E. Ehrlich Ltd.

(57) ABSTRACT

Disclosed are olefin polymerization methods comprising the use of the following compounds:

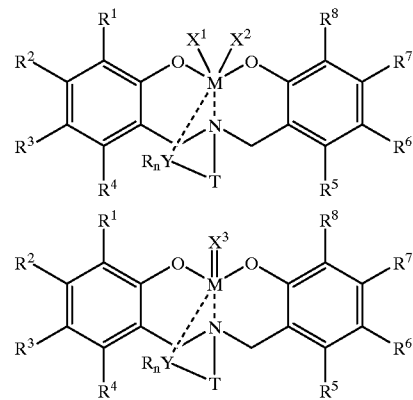

wherein M is a metal atom, $R^1$–$R^8$ are univalent radicals, $X^1$ and $X^2$ are univalent ligands, $X^3$ is a divalent ligand, and ($R_n$Y—T) is an optional donor or non-donor group. The relatively stable and simply synthesized pre-catalyst is activated by a co-catalyst under mild reaction conditions, producing exceptionally reactive polymerization of a wide variety of alpha-olefin monomers, and forming a variety of poly(alpha-olefin) products, having high molecular weight and low molecular weight distribution (PDIs close to 1). Living polymerization is performed at or above room temperature, along with achieving block co-polymerization of alpha-olefin monomers at room temperature, and producing polymers and oligomers having a wide range of molecular weights. The catalyst formed during reaction remains 'alive' for as long as 31 hours, for producing a polymer with a molecular weight as high as 450,000 grams/mole.

130 Claims, 2 Drawing Sheets

METHOD FOR CATALYTIC POLYMERIZATION OF ALPHA-OLEFIN MONOMERS USING AN ULTRA-HIGH ACTIVITY NON-METALLOCENE PRE-CATALYST

This is a Continuation-in-Part of U.S. patent application Ser. No. 09/394,280, filed Sep. 10, 1999, now U.S Pat. No. 6,333,423 entitled: "Ultra-High Activity Non-Metallocene Pre-Catalyst And Method For Catalytic Polymerization Of Alpha-Olefin Monomers".

FIELD AND BACKGROUND OF THE INVENTION

The present invention relates to catalytic polymerization of alpha-olefins, and more particularly, to a method for catalytic polymerization of alpha-olefin monomers using an ultra-high activity non-metallocene pre-catalyst featuring an amine bis(phenolate) ligand-metal chelate.

Currently, there is significant interest relating to methods and systems of catalytic polymerization of alpha-olefin monomers based on a 'pre-catalyst' featuring a metal bound to one or more spectator ligands, where the pre-catalyst may be soluble in a liquid phase solvent, or is adsorbed on a solid surface, and where alpha-olefin monomer reactant may be liquid or gas phase. In such methods and systems, typically, the pre-catalyst is activated by at least one 'co-catalyst', where the combination of the activated pre-catalyst and the at least one co-catalyst functions as a single chemical entity, or complex 'catalyst', for polymerization of the alpha-olefin monomer. The field of catalytic polymerization of alpha-olefin monomers is of significant industrial importance, as more than 50 million tons of poly(alpha-olefin) products, such as polyetheylenes and polypropylenes, are produced each year, involving metal based catalytic processes and systems.

Hereinafter, the term 'pre-catalyst' refers to a chemical entity, in general, and to a chemical compound, in particular, which, when activated by at least one 'co-catalyst', becomes part of a 'catalyst' functional for catalytic polymerization of an alpha-olefin monomer, under proper polymerization reaction conditions. In general, without the presence of at least one co-catalyst, a pre-catalyst is ineffective for catalytic polymerization of an alpha-olefin monomer, and consequently exhibits essentially no catalytic activity for polymerization of an alpha-olefin monomer. Here, when referring to catalytic activity during a polymerization reaction, reference is with respect to the catalytic activity of a pre-catalyst, and it is to be understood that the pre-catalyst functions in concert with at least one co-catalyst for effecting catalytic polymerization of an alpha-olefin monomer. It is noted, however, that there are rare exceptions of a particular pre-catalyst functioning without first being activated by a co-catalyst, for effecting catalytic polymerization of an alpha-olefin monomer. Thus, the present invention focuses on a new and novel pre-catalyst compared to pre-catalysts currently used for catalytic polymerization of alpha-olefin monomers.

Currently, one of the major goals in this field is to produce a variety of new types of poly(alpha-olefin) products, for example, polymers made from alpha-olefin monomers featuring more than two carbon atoms, having well defined bulk or global physicochemical properties, such as mechanical strength, elasticity, melting point, and chemical resistance, applicable for manufacturing a diversity of end products. This may be achieved by controlling the polymer tacticity and polymerizing different types of alpha-olefin monomers, in order to produce a variety of homo-polymers and co-polymers, with varying degrees of monomer incorporation.

Typically, degree of monomer incorporation strongly depends upon catalyst activity for polymerization of a given alpha-olefin monomer. Recently, Britovsek, G. J. P., et al., in "The Search For New-Generation Olefin Polymerization Catalysts: Life Beyond Metallocenes", Angew. Chem. Int. Ed. Engl. 38, 428–447, 1999, provided a practical quantitative ranking of catalytic activity, with respect to weight of a pre-catalyst, (grams polymer produced)/(mmole-pre-cat. hr), for ethylene polymerization, under one bar pressure, as follows: very low<1, low 1–10, moderate 10–100, high 100–1000, very high>1000. Their ranking is derived from data of catalytic polymerization of ethylene, which is the easiest alpha-olefin monomer to polymerize. Catalytic activity for polymerization of other larger alpha-olefin monomers, such as 1-hexene and 1-octene, is usually at least one order of magnitude less. Thus, a pre-catalyst for polymerization of 1-hexene, for example, may be considered exhibiting high, and very high, activity in the range of about 10–100, and 100–1000, grams/(mmole-pre-cat. hr), respectively.

Bulk or global physicochemical properties of polymers are directly related to, and are controllable by, molecular or local physicochemical characteristics of the polymer units making up the bulk polymer. Two notable molecular physicochemical characteristics are polymer molecular weight and polymer molecular weight distribution.

Polymer molecular weight and polymer molecular weight distribution are highly relevant with respect to producing different types of polymers. For example, ultra-high molecular weight polyethylene (UHMWPE), having an average molecular weight above 3,000,000, has the highest abrasion resistance of thermoplastics and a low coefficient of friction. Unlike synthesis of small molecules, however, polymerization reactions involve random events characterized by formation of polymer chains having a range of molecular weights, rather than a single molecular weight. Typically, polymers are better defined and characterized in relation to narrow molecular weight ranges.

The accepted parameter for defining polymer molecular weight distribution is the polydispersity index (PDI), which is the weight average molecular weight, $M_w$, divided by the number average molecular weight, $M_n$, or, $M_w/M_n$. Depending upon the actual application, ideally, a catalytic polymerization system features 'living' polymerization in which the rate of initiation is higher than the rate of propagation, involving a single catalytic active site, and the rate of termination reactions is negligible relative to propagation, thus, leading to a PDI of close to 1. This has been achieved in very few systems for catalytic polymerization of alpha-olefin monomers. A PDI of 2.0, signifying 'non-living' polymerization, is often found in metallocene catalytic systems, also involving a single catalytic active site. Classical heterogeneous Ziegler-Natta catalytic systems usually lead to a broader range of molecular weights with a PDI of about 5. One current challenge is to design alpha-olefin polymerization pre-catalysts, and catalytic systems including such pre-catalysts, leading to poly(alpha-olefin) products with low values of PDI.

Metallocene pre-catalysts, featuring a metal complex including a metal atom, for example from Group IV transition elements such as titanium, zirconium, and hafnium, bound to two ligands from the well known cyclopentadienyl (Cp) family of ligands such as pentamethylcyclopentadienyl, indenyl, or fluorenyl, were introduced during the last two decades for the purpose of catalytic polymerization of alpha-olefin monomers. The most common type of metallocene pre-catalyst is a neutral complex including a metal in oxidation state of +4, bound to two anionic ligands in addition to two standard Cp ligands, for example, bis(cyclopentadienyl)titanium dichloride, also known as titanocene dichloride. A particular group of metallocene pre-catalysts is known as ansa-metallocene complexes, in which the two Cp type ligands are covalently bonded to each other. A related group of complexes is 'constrained geometry' pre-catalysts, featuring a metal bound to both a single Cp type ligand and a second anionic group, where the Cp ligand and second anionic group are covalently bonded to each other.

Using metallocene and metallocene type pre-catalysts in catalytic processes and systems for polymerization of alpha-olefin monomers affords better control of molecular weight and narrower molecular weight distribution, associated with lower values of PDI, relative to the classical Ziegler-Natta family of pre-catalysts such as titanium trichloride using a trialkyl-aluminum co-catalyst. Metallocene and metallocene type pre-catalysts, processes, and systems are well known and taught about in the art. These pre-catalysts, processes and systems are, however, limited in many respects relating to the above discussion.

Foremost, with respect to catalytic activity, metallocene type pre-catalysts typically exhibit relatively moderate activity for polymerizing a small variety of alpha-olefin monomers. With respect to poly(alpha-olefin) product types and variety, alpha-olefin monomers polymerized by metallocene pre-catalysts are mostly short chain ethylene and propylene, which are already well taught about. Metallocene pre-catalysts are limited in terms of availability and versatility. Metallocene type pre-catalysts are relatively difficult to synthesize, a fact which limits the possibility of developing new varieties of metallocene type alpha-olefin polymerization pre-catalysts.

Due to continued searching for new poly(alpha-olefin) products exhibiting selected well defined bulk physico-chemical properties and molecular physicochemical characteristics, combined with the above limitations associated with metallocene pre-catalysts, there is growing interest in developing non-metallocene alpha-olefin polymerization pre-catalysts, and related catalytic processes, and systems. The main emphasis is on obtaining new alpha-olefin polymerization pre-catalysts which are readily available, exhibit relatively high stability, and can be used for improving control over industrially important polymer parameters such as molecular weight, molecular weight distribution, product type, and variety.

The first step towards development of non-metallocene pre-catalysts was taken by the introduction of a 'half sandwich' pre-catalyst, featuring a complex including a Cp type ligand bridging to a heteroatom donor. An example of such a pre-catalyst is a phenolate constrained geometry polymerization pre-catalyst disclosed in U.S. Pat. No. 5,856,258. The pre-catalyst described therein shows relatively high activity of about 1,300 grams/(mmole-pre-cat. hr) for polymerization of alpha-olefin monomers, however monomers polymerized are limited to ethylene, propylene, and styrene.

A non-metallocene alpha-olefin polymerization catalytic system is disclosed in U.S. Pat. No. 5,852,146, and features a bis(hydroxy aromatic nitrogen ligand) transition metal pre-catalyst, functioning with an activating methylaminoxane (MAO) co-catalyst. Relatively high catalytic activity of about 4,000 grams/(mmole-pre-cat. hr) is reported for polymerization of ethylene only. Moreover, MAO is needed in large quantities as co-catalyst, which, in general poses notable limitations relating to cost and containment. MAO used in large quantities is costly, and needs to be properly disposed of with regard to environmental considerations.

Living polymerization of 1-hexene is recently described by Schrock, R. R., in *J. Am. Chem. Soc.* 119, 3830, 1997, and is disclosed in U.S. Pat. No. 5,889,128. One of the non-metallocene pre-catalyst compositions described therein comprises a dimethyl complex in which the metal atom is chelated to a tridentate spectator ligand, which is activated by a non-MAO boron salt co-catalyst. Catalytic activity under the conditions described was considered high, of about 200 grams/(mmole-pre-cat. hr), and the molecular weight of the obtained poly(1-hexene) product is moderate, of about 50,000 grams/mole.

Living polymerization of 1-hexene is also described by McConville, D. H., in *J Am. Chem. Soc.* 118, 10008, 1996. They describe a moderately active non-metallocene polymerization pre-catalyst, exhibiting activity of about 40 g/(mmole-pre-cat. hr), involving activation of a pre-catalyst featuring a dimethyl metal complex of a bis(amide) ligand, with a non-MAO boron Lewis acid as co-catalyst under room temperature, for producing a moderate molecular weight polymer, of molecular weight of 40,000 grams/mole. The same pre-catalyst, but functioning with MAO as co-catalyst in large excess, under the same reaction conditions, yields significantly higher activity, as reported by McConville, D. H., in *Macromolecules V.* 29, 5241, 1996. Again, limitations associated with using MAO as co-catalyst are present.

Another active non-metallocene living 1-hexene polymerization pre-catalyst functioning with a non-MAO co-catalyst, is reported by Kim, K., in *Organometallics* 17, 3161, 1998. The described catalyst system exhibits activity of about 400 grams/(mmole-pre-cat. hr).

A non-metallocene non-living 1-hexene polymerization pre-catalyst is disclosed in U.S. Pat. No. 5,807,801. The pre-catalyst exhibits high activity, of on the order of $10^6$ g/(mmole-pre-cat. hr), when the pre-catalyst is, again, activated with MAO as co-catalyst, for the polymerization process taking place at 50° C.

A non-metallocene bis(phenolate) pre-catalyst is reported by Schaverien, C. J., in *J. Am. Chem. Soc.* 117, 3008, 1995. The pre-catalyst described exhibits limited activity, of about 10 g/(mmole-pre-cat. hr), for tactic polymerization of 1-hexene, yielding high molecular weight isotactic poly(1-hexene).

A potentially important industrial application of living polymerization of alpha-olefin monomers is the synthesis of block copolymers. This requires either total or nearly total consumption of the first monomer to produce a narrow PDI fragment before addition of the second monomer, upon which the polymerization process should resume. These requirements are extremely difficult to attain, and therefore it is no surprise that despite the intensive efforts invested in the field of alpha-olefin polymerization, very few systems that induce living polymerization of alpha-olefin monomers are known to be applicable for producing block co-polymers. Moreover, all such prior art polymerization systems operate below room temperature (25° C.).

In view of the above discussed limitations for polymerization of alpha-olefins, to one of ordinary skill in the art, there is thus a need for, and it would be highly advantageous to have a method for catalytic polymerization of alpha-olefin monomers using an ultra-high activity non-metallocene pre-catalyst, where the pre-catalyst is not limited to activation by large quantities of a co-catalyst such as MAO, is characterized by high stability, and is readily obtained or synthesized. There is also a need for such a method of polymerization which is capable of producing different types and varieties of poly(alpha-olefin) products having high molecular weight, and low molecular weight distribution, of being performed at and above room temperature, of exhibiting living polymerization at and above room temperature, and, of producing block copolymers. Moreover, there is a need for such a method using the pre-catalyst for producing alpha-olefin polymers other than polyethylenes and polypropylenes, having industrially applicable properties and characteristics.

SUMMARY OF THE INVENTION

The present invention relates to a method for catalytic polymerization of alpha-olefin monomers using an ultra-high activity non-metallocene pre-catalyst featuring an amine bis(phenolate) ligand-metal chelate.

Thus, according to the present invention, there is provided a method for catalytic polymerization of an alpha-olefin monomer comprising the steps of: (a) providing a particular form of an amine bis(phenolate) pre-catalyst having a general structure selected from the group consisting of:

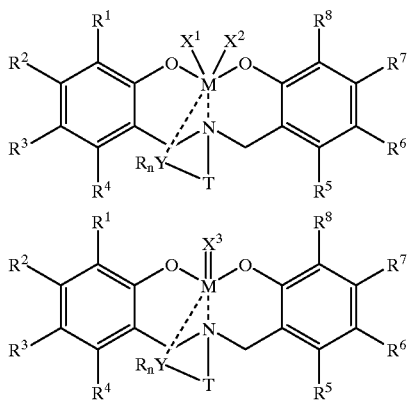

wherein: a solid line represents a covalent bond; a dashed line represents a bond having a varying degree of covalency and a varying degree of coordination; M is a metal atom covalently bonded to each O atom and bonded with varying degrees of covalency and coordination to the N atom; $X^1$ and $X^2$ are each a univalent anionic ligand covalently bonded to the metal atom; $X^3$ is a single divalent anionic ligand covalently bonded to the metal atom; $R^1$ through $R^4$ are each a univalent radical covalently bonded to first ($C_6$) aromatic group; $R^5$ through $R^8$ are each a univalent radical covalently bonded to second ($C_6$) aromatic group; and ($R_n$Y—T) is an optional group selected from the group consisting of a non-donor group covalently bonded to the N atom, wherein the non-donor group, the T is a covalent bridging group between the N atom and the Y, the Y is a group covalently bonded to the T, and, each of at least one $R_n$ is selected from the group consisting of a saturated substituent covalently bonded to the Y, an unsaturated substituent covalently bonded to the Y, and a univalent radical covalently bonded to the Y, and a donor group covalently bonded to the N atom, wherein the donor group, the T is a covalent bridging group between the N atom and the Y, the Y is a heteroatom covalently bonded to the T and bonded with varying degrees of covalency and coordination to the metal atom, and, optional $R_n$ substituents are selected from the group consisting of at least one saturated substituent covalently bonded to the Y, and at least one unsaturated substituent covalently bonded to the Y; (b) preparing a first chemical entity featuring the particular form of the amine bis (phenolate) pre-catalyst of step (a); (c) providing a co-catalyst suitable for activating the particular form of the amine bis(phenolate) pre-catalyst; (d) preparing a second chemical entity featuring the provided co-catalyst of step (c); (e) forming a catalytic polymerization reaction by mixing (i) the first chemical entity featuring the particular form of the amine bis(phenolate) pre-catalyst, with (ii) the second chemical entity of the provided co-catalyst, with (iii) the alpha-olefin monomer to be catalytically polymerized, whereby the co-catalyst activates the pre-catalyst, whereby combination of the pre-catalyst and the co-catalyst becomes a catalyst for effecting the catalytic polymerization of the alpha-olefin monomer and for producing at least one poly (alpha-olefin) product; (f) allowing the catalytic polymerization reaction to progress; (g) terminating the catalytic polymerization reaction; and (h) isolating the at least one poly(alpha-olefin) product formed by the catalytic polymerization reaction.

According to another aspect of the present invention, there is provided a method for catalytic polymerization of an alpha-olefin monomer comprising the steps of: (a) providing a particular form of an amine bis(phenolate) catalyst having a general structure selected from the group consisting of:

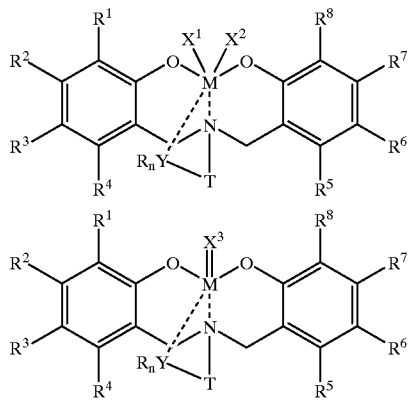

wherein: a solid line represents a covalent bond; a dashed line represents a bond having a varying degree of covalency and a varying degree of coordination; M is a metal atom covalently bonded to each O atom and bonded with varying degrees of covalency and coordination to the N atom; $X^1$ and $X^2$ are each a univalent anionic ligand covalently bonded to the metal atom; $X^3$ is a single divalent anionic ligand covalently bonded to the metal atom; $R^1$ through $R^4$ are each a univalent radical covalently bonded to first ($C_6$) aromatic group; $R^5$ through $R^8$ are each a univalent radical covalently bonded to second ($C_6$) aromatic group; and ($R_n$Y—T) is an optional group selected from the group consisting of a non-donor group covalently bonded to the N atom, wherein the non-donor group, the T is a covalent bridging group between the N atom and the Y, the Y is a group covalently bonded to the T, and, each of at least one $R_n$ is selected from the group consisting of a saturated substituent covalently bonded to the Y, an unsaturated substituent covalently bonded to the Y, and a univalent radical covalently bonded to the Y, and a donor group covalently bonded to the N atom, wherein the donor group, the T is a covalent bridging group between the N atom and the Y, the Y is a heteroatom covalently bonded to the T and bonded with varying degrees of covalency and coordination to the metal atom, and, optional $R_n$ substituents are selected from the group consisting of at least one saturated substituent covalently bonded to the Y, and at least one unsaturated substituent covalently bonded to the Y; (b) preparing a first chemical entity featuring the particular form of the amine bis (phenolate) catalyst of step (a); (c) forming a catalytic polymerization reaction by mixing (i) the first chemical entity featuring the particular form of the amine bis (phenolate) catalyst, with (ii) the alpha-olefin monomer to be catalytically polymerized, whereby the amine bis (phenolate) catalyst effects the catalytic polymerization of the alpha-olefin monomer for producing at least one poly (alpha-olefin) product; (d) allowing the catalytic polymerization reaction to progress; (e) terminating the catalytic polymerization reaction; and (f) isolating the at least one poly(alpha-olefin) product formed by the catalytic polymerization reaction.

According to another aspect of the present invention, there is provided a method for living catalytic polymerization of an alpha-olefin monomer comprising the steps of: (a) providing a particular form of an amine bis(phenolate) pre-catalyst having a general structure selected from the group consisting of:

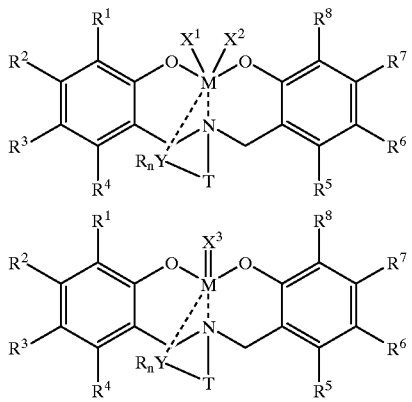

wherein: a solid line represents a covalent bond; a dashed line represents a bond having a varying degree of covalency and a varying degree of coordination; M is a metal atom covalently bonded to each O atom and bonded with varying degrees of covalency and coordination to the N atom; $X^1$ and $X^2$ are each a univalent anionic ligand covalently bonded to the metal atom; $X^3$ is a single divalent anionic ligand covalently bonded to the metal atom; $R^1$ through $R^4$ are each a univalent radical covalently bonded to first ($C_6$) aromatic group; $R^5$ through $R^8$ are each a univalent radical covalently bonded to second ($C_6$) aromatic group; and ($R_n Y$—T) is an optional group selected from the group consisting of a non-donor group covalently bonded to the N atom, wherein the non-donor group, the T is a covalent bridging group between the N atom and the Y, the Y is a group covalently bonded to the T, and, each of at least one $R_n$ is selected from the group consisting of a saturated substituent covalently bonded to the Y, an unsaturated substituent covalently bonded to the Y, and a univalent radical covalently bonded to the Y, and a donor group covalently bonded to the N atom, wherein the donor group, the T is a covalent bridging group between the N atom and the Y, the Y is a heteroatom covalently bonded to the T and bonded with varying degrees of covalency and coordination to the metal atom, and, optional $R_n$ substituents are selected from the group consisting of at least one saturated substituent covalently bonded to the Y, and at least one unsaturated substituent covalently bonded to the Y; (b) preparing a first chemical entity featuring the particular form of the amine bis (phenolate) pre-catalyst of step (a); (c) providing a co-catalyst suitable for activating the particular form of the amine bis(phenolate) pre-catalyst; (d) preparing a second chemical entity featuring the provided co-catalyst of step (c); (e) forming a living catalytic polymerization reaction by mixing (i) the first chemical entity featuring the particular form of the amine bis(phenolate) pre-catalyst, with (ii) the second chemical entity of the provided co-catalyst, with (iii) the alpha-olefin monomer to be catalytically polymerized, whereby the co-catalyst activates the pre-catalyst, whereby combination of the pre-catalyst and the co-catalyst becomes a catalyst for effecting the living catalytic polymerization of the alpha-olefin monomer and for producing at least one poly(alpha-olefin) product; (f) allowing the living catalytic polymerization reaction to progress; (g) terminating the living catalytic polymerization reaction; and (h) isolating the at least one poly(alpha-olefin) product formed by the living catalytic polymerization reaction.

The amine bis(phenolate) ligand-metal chelate pre-catalyst of the present invention, when activated by a co-catalyst under mild reaction conditions, is exceptionally reactive for polymerization of a variety of alpha-olefin monomers, including long chain alpha-olefin monomers such as 1-hexene or 1-octene, for forming a variety of poly(alpha-olefin) products such as poly(1-hexene) or poly (1-octene), having high molecular weight and low molecular weight distribution. The amine bis(phenolate) ligand-metal chelate pre-catalyst is relatively stable under commercially applicable conditions for polymerization of alpha-olefin monomers. Moreover, the pre-catalyst, and related forms of the pre-catalyst, of the present invention are relatively simple to synthesize, primarily due to simple syntheses of the corresponding amine bis(2-hydroxyarylmethyl) ligand precursors from a variety of commercially available inexpensive starting materials, compared to syntheses of metallocene type pre-catalysts.

Several additional particular novelties and advantages provided by the method of the present invention for polymerization of alpha-olefin monomers, are briefly listed herein:

(a) The described method is implemented for providing living polymerization performed under the very rare conditions of room temperature (25° C.), characterized by a very narrow polydispersity index (PDI) of close to 1.0.

(b) The described method is implemented by appropriately activating the disclosed non-metallocene pre-catalyst, for forming a catalyst which remains 'alive' for an exceptionally long period of time, of as long as 31 hours, whereby, there is producing 'in a living fashion' a polymer having exceptionally high molecular weight of as high as 450,000 grams/mole.

(c) The described method is implemented for providing living polymerization of alpha-olefin monomers 'above' room temperature, by using a particular pre-catalyst from the disclosed non-metallocene pre-catalyst family.

(d) The described method, using the disclosed pre-catalyst applicable for living polymerization, is implemented for achieving block co-polymerization of alpha-olefin monomers conducted at room temperature. After employing one monomer, which is either totally or nearly totally consumed in a living fashion, a second monomer is added, yielding a block co-polymer.

(e) The described method is implemented for the polymerization of a variety of monomers, such as 1-hexene, 1-octene, 1,5-hexadiene, and the ones of highest industrial significance: propylene and ethylene.

(f) The described method is implemented for producing polymers having a wide range of molecular weights. In particular, there is producing polymers having molecular weights of as high as 450,000 grams/mole, as well as oligomers with molecular weights of 1000 grams/mole.

(g) The described method is implemented for providing a variety of reactivities, by varying the amine bis(phenolate) ligand and the metal, with varying degrees of exotherm, which contributes to controlling reaction temperature.

(h) The described method is implemented for synthesizing hyper-branched polymers, through production of high olefin oligomers having terminal olefinic groups, and their further polymerization.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
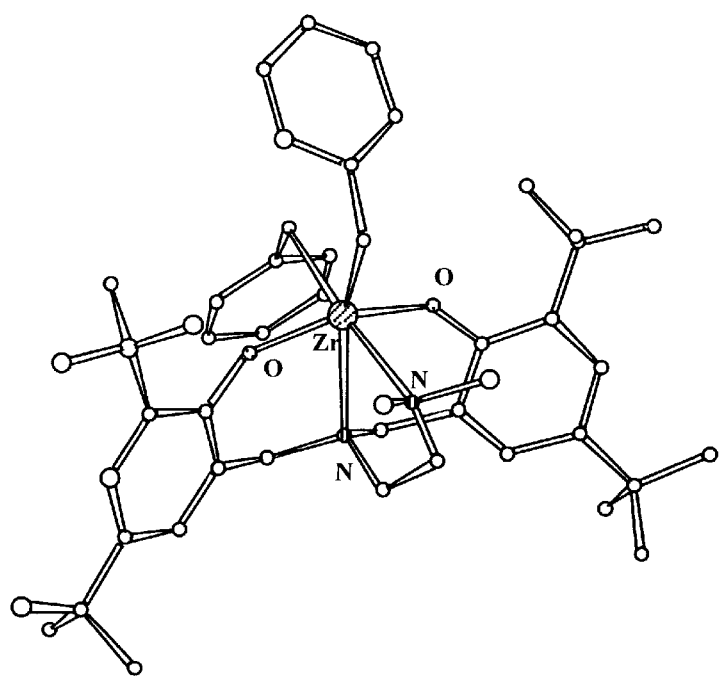
FIG. 1 is an illustration of the X-ray structure of six coordinate dialkyl amine bis(phenolate) ligand-metal chelate pre-catalyst [(CH$_3$)$_2$N—CH$_2$—CH$_2$—]—Zr(CH$_2$Ph)$_2$ 9.

The present invention relates to a method for catalytic polymerization of alpha-olefin monomers using an ultra-high activity non-metallocene pre-catalyst featuring an amine bis(phenolate) ligand-metal chelate.

The amine bis(phenolate) ligand-metal chelate pre-catalyst of the present invention, when activated by a co-catalyst under mild reaction conditions, is at least one order of magnitude more reactive for polymerization of a variety of alpha-olefin monomers compared to polymerization of alpha-olefin monomers using metallocene or metallocene type pre-catalysts. The amine bis(phenolate) ligand-metal chelate pre-catalyst polymerizes long chain alpha-olefin monomers such as 1-hexene or 1-octene, for forming a variety of poly(alpha-olefin) products such as poly(1-hexene) or poly(1-octene), having high molecular weight and low molecular weight distribution. The amine bis (phenolate) ligand-metal chelate pre-catalyst is relatively stable under commercially applicable conditions for polymerization of alpha-olefin monomers. Moreover, this pre-catalyst is relatively simple to synthesize, and is considered more available compared to currently used metallocene type pre-catalysts.

It is to be understood that the invention is not limited in its application with respect to details of exemplary chemical structures, formulas, methods, procedures, and, order or sequence of steps of implementing the described methods, set forth in the following description, drawings, or examples. For example, an alpha-olefin monomer selected from the group consisting of ethylene, propylene, 1-pentene, 1-hexene, 1-octene, and, 1,5-hexadiene, is referred to in the following description and in one or more of the Examples of the method. It is to be clearly understood that other alpha-olefin monomers, such as higher alpha-olefin monomers, not indicated herein, can be used for implementing the disclosed method. Additionally, for example, the following description refers to room temperature as 25° C., as it is well known in the art, in order to illustrate implementation of the present invention. It is to be clearly understood that, herein, room temperature refers to the temperature range of from about 20° C. to about 30° C., and refers preferably to the temperature of 25° C.

Accordingly, the invention is capable of other embodiments or of being practiced or carried out in various ways. Also, it is to be understood that the phraseology and terminology employed herein is for the purpose of description and should not be regarded as limiting.

General Structures And Formulas Of The Amine Bis (phenolate) Ligand-Metal Chelate Pre-catalyst. The preferred embodiment of the amine bis(phenolate) ligand-metal chelate pre-catalyst of the present invention is either general structure 1 or general structure 2:

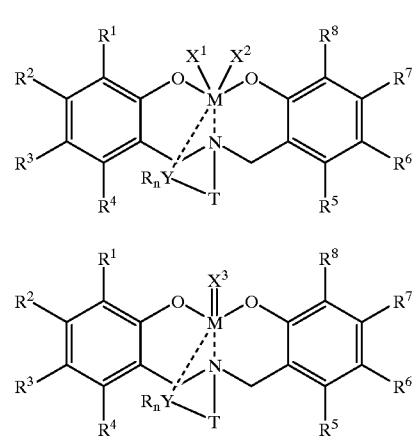

wherein a solid line represents a covalent bond and a dashed line represents a bond varying in degree of covalency and coordination between the indicated atoms; 'M' is a metal atom covalently bonded to each O atom and bonded with varying degrees of covalency and coordination to the N atom, as shown in structures 1 and 2 by the dashed line between the metal atom, M, and the N atom, such as a transition metal atom including zirconium, hafnium or titanium; X$^1$ and X$^2$ are each a univalent anionic ligand covalently bonded to the metal atom, M, such as a halide, a hydride, a saturated or unsaturated hydrocarbyl, an alkoxide, an aryloxide, a dialkylamide, or an arylamide; R$^1$ through R$^4$ are each a univalent radical covalently bonded to the first (C$_6$) aromatic group, such as a hydrogen, hydrocarbyl, or any other univalent radical like an alkoxide; R$^5$ through R$^8$ are each a univalent radical covalently bonded to the second (C$_6$) aromatic group, such as a hydrogen, hydrocarbyl, or any other univalent radical like an alkoxide.

(R$_n$Y—T) is an optional group in each of the two general structures 1 and 2, and is selected from the group consisting of a non-donor group covalently bonded to the N atom, where, in the non-donor group, 'T' is a covalent bridging group between the N atom and 'Y', such as a saturated hydrocarbyl, or an unsaturated hydrocarbyl, 'Y' is a group covalently bonded to T such as a saturated hydrocarbyl or an unsaturated hydrocarbyl, and, each of at least one $R_n$ is selected from the group consisting of a saturated substituent covalently bonded to Y, such as a methyl substituent or an ethyl substituent, an unsaturated substituent covalently bonded to Y, and a univalent radical covalently bonded to Y, such as a hydrogen radical or a methyl radical, and a donor group covalently bonded to the N atom, where, in the donor group, 'T' is a covalent bridging group between the N atom and 'Y', such as a saturated hydrocarbyl, an unsaturated hydrocarbyl, or a part of an aromatic system such as pyridine, 'Y' is a heteroatom covalently bonded to T and bonded with varying degrees of covalency and coordination to the metal atom, M, as shown in structures 1 and 2 by the dashed line between Y and the metal atom, M, such as nitrogen, oxygen, sulfur or phosphorous, and, optional $R_n$ substituents are selected from the group consisting of at least one saturated substituent covalently bonded to Y, such as a methyl or an ethyl substituent, and at least one unsaturated substituent covalently bonded to Y, such as part of an aromatic system.

In the case that the group ($R_n$Y—T) is not present in either general structure 1 or 2 of the pre-catalyst of the present invention, the metal atom, M, is capable of forming a pure covalent bond to the N atom, whereby, the dashed line is replaced by a solid line between metal atom, M, and the N atom.

In an alternative preferred embodiment of the general structure of the amine bis(phenolate) ligand-metal chelate pre-catalyst 1 of the present invention, univalent anionic ligands $X^1$ and $X^2$ are replaced by ligand $X^3$, a single divalent anionic ligand covalently bonded to the metal, M, such as a cyclometallated hydrocarbyl, or a radical such as an alkylidene, resulting in alternative general structure of the amine bis(phenolate) ligand-metal chelate pre-catalyst 2 of the present invention.

General formulas corresponding to general structures 1 and 2 of amine bis(phenolate) ligand-metal chelate pre-catalyst of the present invention are as follows: [{(O)$^1$R$^1$R$^2$R$^3$R$^4$(C$_6$)$^1$(CH$_2$)$^1$(R$_n$Y—T)N(CH$_2$)$^2$(C$_6$)$^2$R$^5$R$^6$R$^7$R$^8$(O)$^2$}MX$^1$X$^2$] and [{(O)$^1$R$^1$R$^2$R$^3$R$^4$(C$_6$)$^1$(CH$_2$)$^1$(R$_n$Y—T)N(CH$_2$)$^2$(C$_6$)$^2$R$^5$R$^6$R$^7$R$^8$(O)$^2$}MX$^3$], respectively.

As previously described with respect to general structures 1 and 2 of the pre-catalyst of the present invention, here, 'M' is a metal atom covalently bonded to each O atom, (O)$^1$ and (O)$^2$, and bonded to the N atom with varying degrees of covalency and coordination, as shown in general structures 1 and 2 by the dashed line between the metal atom, M, and the N atom, such as a transition metal atom including zirconium, hafnium or titanium; $X^1$ and $X^2$ are each a univalent anionic ligand covalently bonded to the metal atom, M, such as a halide, a hydride, a saturated or unsaturated hydrocarbyl, an alkoxide, an aryloxide, an dialkylamide, or an arylamide; $X^3$ is a single divalent anionic ligand covalently bonded to the metal atom, M, such as a cyclometallated hydrocarbyl, or a radical such as an alkylidene; $R^1$ through $R^4$ are each a univalent radical covalently bonded to the first (C$_6$) aromatic group, (C$_6$)$^1$, such as a hydrogen, hydrocarbyl, or any other univalent radical like an alkoxide; $R^5$ through $R^8$ are each a univalent radical covalently bonded to the second (C$_6$) aromatic group, (C$_6$)$^2$, such as a hydrogen, hydrocarbyl, or any other univalent radical like an alkoxide.

($R_n$Y—T) is an optional group in each of the two general structures 1 and 2, and is selected from the group consisting of a non-donor group covalently bonded to the N atom, where, in the non-donor group, 'T' is a covalent bridging group between the N atom and 'Y', such as a saturated hydrocarbyl, or an unsaturated hydrocarbyl, 'Y' is a group covalently bonded to T such as a saturated hydrocarbyl or an unsaturated hydrocarbyl, and, each of at least one $R_n$ is selected from the group consisting of a saturated substituent covalently bonded to Y, such as a methyl substituent or an ethyl substituent, an unsaturated substituent covalently bonded to Y, and a univalent radical covalently bonded to Y, such as a hydrogen radical or a methyl radical, and a donor group covalently bonded to the N atom, where, in the donor group, 'T' is a covalent bridging group between the N atom and 'Y', such as a saturated hydrocarbyl, an unsaturated hydrocarbyl, or a part of an aromatic system such as pyridine, 'Y' is a heteroatom covalently bonded to T and bonded with varying degrees of covalency and coordination to the metal atom, M, as shown in structures 1 and 2 by the dashed line between Y and the metal atom, M, such as nitrogen, oxygen, sulfur or phosphorous, and, optional $R_n$ substituents are selected from the group consisting of at least one saturated substituent covalently bonded to Y, such as a methyl or an ethyl substituent, and at least one unsaturated substituent covalently bonded to Y, such as part of an aromatic system.

In the case that the group ($R_n$Y—T) is not present in either general formula of the pre-catalyst of the present invention, the metal atom, M, is capable of forming a pure covalent bond to the N atom.

Synthesis of amine bis(2-hydroxyarylmethyl), general ligand precursor

Synthesis of the general ligand precursor, amine bis(2-hydroxyarylmethyl) 6, described below and used for synthesizing different related forms of the amine bis(phenolate) ligand-metal chelate pre-catalyst of the present invention, is taught by Burke, W. J. et al., in *J. Org. Chem.* 29, 909, 1964. The inventors synthesized different forms of general ligand precursor 6 using a modified Mannich reaction between a primary amine 3, formaldehyde 4, and substituted phenols 5A and 5B.

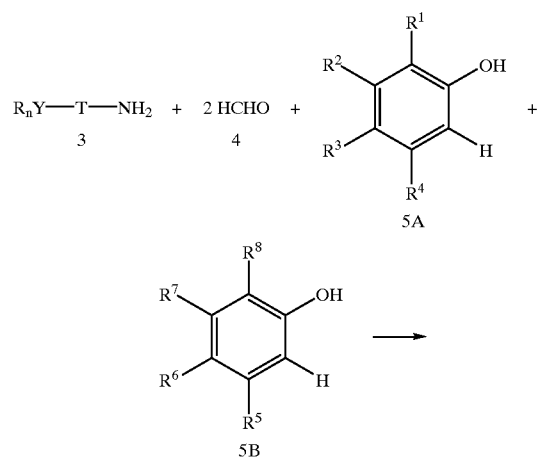

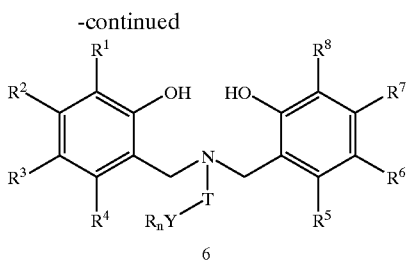

6

The structure of amine bis(2-hydroxyarylmethyl) general ligand precursor 6 features two hydroxyaryl rings, wherein the hydroxyaryl rings include a variety of substituents $R^1$ through $R^8$. Substituents $R^1$ through $R^4$ are each a univalent radical covalently bonded to the first hydroxyaryl ring, such as a hydrogen, hydrocarbyl, or any other univalent radical like an alkoxide, and substituents $R^5$ through $R^8$ are each a univalent radical covalently bonded to the second hydroxyaryl ring, such as a hydrogen, hydrocarbyl, or any other univalent radical like an alkoxide.

The two hydroxyaryl rings are bridged by a bridging group —CH$_2$—($R_n$Y—T)N—CH$_2$—. The bridging group, —CH$_2$—($R_n$Y—T)N—CH$_2$—, includes the group ($R_n$Y—T), wherein as described above, ($R_n$Y—T) is either of two general forms, and is selected from the group consisting of a non-donor group covalently bonded to the N atom, where, in the non-donor group, 'T' is a covalent bridging group between the N atom and 'Y', such as a saturated hydrocarbyl, or an unsaturated hydrocarbyl, 'Y' is a group covalently bonded to T such as a saturated hydrocarbyl or an unsaturated hydrocarbyl, and, each of at least one $R_n$ is selected from the group consisting of a saturated substituent covalently bonded to Y, such as a methyl substituent or an ethyl substituent, an unsaturated substituent covalently bonded to Y, and a univalent radical covalently bonded to Y, such as a hydrogen radical or a methyl radical, and a donor group covalently bonded to the N atom, where, in the donor group, T is a covalent bridging group between the N atom and Y, such as a saturated hydrocarbyl, an unsaturated hydrocarbyl, or a part of an aromatic system such as pyridine, Y is a heteroatom covalently bonded to T, such as nitrogen, oxygen, sulfur or phosphorous, and, optional $R_n$ substituents are selected from the group consisting of at least one saturated substituent covalently bonded to Y, such as a methyl substituent or an ethyl substituent, and at least one unsaturated substituent covalently bonded to Y, such as part of an aromatic system, for example, pyridine. Each different form of the group ($R_n$Y—T) covalently bonded to the N atom, typically extends from the N atom with a different characteristic length.

Three specific examples of the bridging group, —CH$_2$—($R_n$Y—T)N—CH$_2$—, each including a different form of the optional group ($R_n$Y—T), are (i) where ($R_n$Y—T) is the donor group [(CH$_3$)$_2$N—CH$_2$—CH$_2$—], wherein T is saturated hydrocarbyl, —CH$_2$—CH$_2$—, covalently bonded to the N atom of the bridging group and covalently bonded to Y, where Y is heteroatom N, and two $R_n$ saturated substituents are two methyl substituents, (—CH$_3$)$_2$, each covalently bonded to donor group N atom; (ii) where ($R_n$Y—T) is the non-donor group [CH$_3$—CH$_2$—CH$_2$—], without a heteroatom, wherein T is saturated hydrocarbyl, —CH$_2$—CH$_2$—, covalently bonded to the N atom of the bridging group and covalently bonded to Y, Y is methylene group, —CH$_2$—, and a single $R_n$ substituent is a hydrogen radical covalently bonded to the methylene group; and, (iii) where ($R_n$Y—T) is the donor group [(C$_5$H$_4$N)—CH$_2$—], wherein T is unsaturated hydrocarbyl, —CH$_2$—C—, covalently bonded to the N atom of the bridging group and covalently bonded to Y, and, Y is heteroatom N, which along with a single four-carbon $R_n$ substituent form part of a pyridine aromatic ring system, where pyridine is covalently bonded to the —CH$_2$— part of T, via carbon at pyridine position number 2. Details of the syntheses and spectroscopic data of the resulting structures of different forms of the amine bis(2-hydroxyarylmethyl) general ligand precursor 6, corresponding to each exemplary form of the bridging group including a different form of the group ($R_n$Y—T) are provided in Examples 1, 2, and 3, respectively, below.

Synthesis of amine bis(phenolate) ligand-metal chelate pre-catalysts. Amine bis(2-hydroxyarylmethyl) general ligand precursor 6 is targeted for binding to a metal, such as a transition metal including zirconium, titanium, and hafnium, for synthesizing different forms of amine bis(phenolate) ligand-metal chelate pre-catalyst 1 or 2, in accordance to the above descriptions. Amine bis(2-hydroxyarylmethyl) general ligand precursor 6 reacts, under variable reaction conditions, with one equivalent of a transition metal complex such as zirconium tetra(benzyl), zirconium tetrakis(dimethylamide), titanium tetra (isopropoxide) or hafnium tetra(chloride), to yield the bis(phenolate) zirconium dibenzyl complex, the bis(phenolate) zirconium bis(dimethylamide) complex, the bis(phenolate) titanium bis(isopropoxide) complex, and the bis(phenolate) hafnium dichloride complex, respectively.

Each complex thus formed may be used directly as a pre-catalyst for polymerization of an alpha-olefin monomer, or may be transformed into a pre-catalyst by chemical transformation, such as transformation of amine bis(phenolate) titanium bis(isopropoxide) into amine bis(phenolate) titanium dichloride using a variety of chlorinating reagents, such as trimethylsilylchloride or triethylamine hydrochloride. The amine bis(phenolate) titanium dichloride may be further transformed into an amine bis(phenolate) titanium dialkyl using a variety of alkylating reagents, such as benzyl magnesium chloride or methyl magnesium bromide.

Synthesis of three exemplary forms of the amine bis(phenolate) ligand-metal chelate pre-catalyst 1 of the present invention, where, in particular, the metal atom, M, is the transition metal zirconium (Zr), are generally described here. These exemplary forms of pre-catalyst 1 are distinguished by including a different form of the optional ($R_n$Y—T) group, and are referenced with respect to the ($R_n$Y—T) group. Further details of each synthesis and, spectroscopic and X-ray data of resulting structures are provided in Examples 4, 5, and 6, respectively, below.

Synthesis of first exemplary ligand-metal chelate pre-catalyst, [(CH$_3$)$_2$N—CH$_2$—CH$_2$—]—Zr(CH$_2$Ph)$_2$ 9. For the first exemplary form of chelate pre-catalyst 1, amine bis(2-hydroxyarylmethyl) specific ligand precursor 7, referenced hereinafter as ligand precursor [(CH$_3$)$_2$N—CH$_2$—CH$_2$—] 7, is derived from reaction (not shown) of NN-dimethylethylenediamine, as a specific form of primary amine 3, with formaldehyde 4 and 2,4-di-tert(butyl)phenol, as a specific form of substituted phenols 5A and 5B. Ligand precursor [(CH$_3$)$_2$N—CH$_2$—CH$_2$—] 7 is a specific form of amine bis(2-hydroxyarylmethyl) general ligand precursor 6, where the bridging group, —CH$_2$—($R_n$Y—T)N—CH$_2$—, includes ($R_n$Y—T) as donor group, (CH$_3$)$_2$N—CH$_2$—CH$_2$—, wherein T is saturated hydrocarbyl, —CH$_2$—CH$_2$—, covalently bonded to the N atom of the bridging group and covalently bonded to Y, where Y is heteroatom N, and two $R_n$ saturated substituents are two methyl substituents, (—CH$_3$)$_2$, each covalently bonded to donor group N atom.

Ligand precursor [(CH$_3$)$_2$N—CH$_2$—CH$_2$—] 7 reacts cleanly with one equivalent of zirconium tetra(benzyl), Zr(CH$_2$Ph)$_4$ 8, at 65° C. yielding the six coordinate dialkyl amine bis(phenolate) ligand-metal chelate pre-catalyst —9, also referenced as [(CH$_3$)$_2$N—CH$_2$—CH$_2$—]—Zr(CH$_2$Ph)$_2$—9, quantitatively as a yellow crystalline solid.

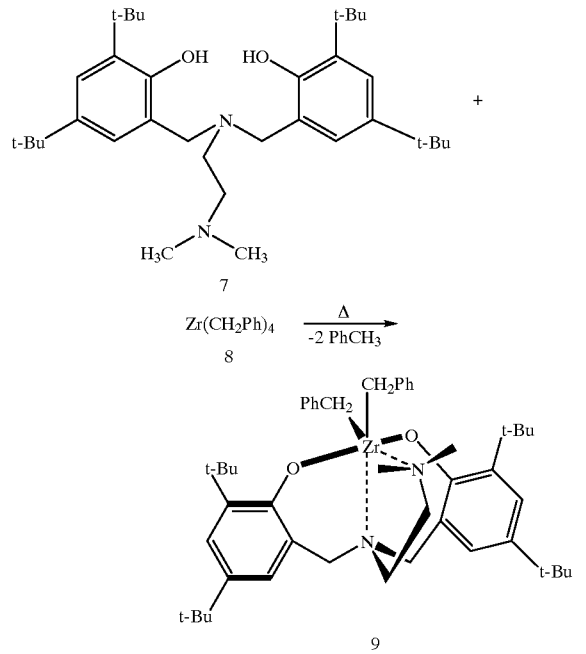

Spectroscopic data of ligand-metal pre-catalyst 9 are consistent with a single stereoisomer featuring symmetrically related phenolate rings, two different benzyl groups, and an AX spin system for the two benzylic methylene groups. This points to a rigid chelate of C$_s$ symmetry on the NMR time scale, with the benzyl groups in a cis geometry, as required for alpha-olefin polymerization catalysts, and the phenolate groups in a trans geometry. The crystallographic (X-ray) structure of pre-catalyst 9 shown in FIG. 1, supports the spectroscopic data, and indicates a structure featuring a mononuclear zirconium chelate having a slightly distorted octahedral geometry, including a coordinative bond between Zr and each of the two nitrogen atoms.

Synthesis of second exemplary ligand-metal chelate pre-catalyst, [CH$_3$—CH$_2$—CH$_2$—]—Zr(CH$_2$Ph)$_2$ 11. For the second exemplary form of chelate pre-catalyst 1, amine bis(2-hydroxyarylmethyl) specific ligand precursor 10, hereinafter referenced as ligand precursor [CH$_3$—CH$_2$—CH$_2$—] 10, is derived from reaction (not shown) of 1-aminopropane, as a specific form of primary amine 3, with formaldehyde 4 and 2,4-di-tert(butyl)phenol, as a specific form of substituted phenols 5A and 5B. Ligand precursor [CH$_3$—CH$_2$—CH$_2$—] 10 is a specific form of amine bis(2-hydroxyarylmethyl) general ligand precursor 6, where the bridging group, —CH$_2$—(R$_n$Y—T)N—CH$_2$—, includes (R$_n$Y—T) as the non-donor group CH$_3$—CH$_2$—CH$_2$—, without a heteroatom, wherein T is saturated hydrocarbyl, —CH$_2$—CH$_2$—, covalently bonded to the N atom of the bridging group and covalently bonded to Y, Y is methylene group, —CH$_2$—, and a single R$_n$ substituent is a hydrogen radical covalently bonded to the methylene group.

Ligand precursor [CH$_3$—CH$_2$—CH$_2$—] 10 reacts cleanly with one equivalent of zirconium tetra(benzyl), Zr(CH$_2$Ph)$_4$ 8, at 65° C. yielding the five coordinate dialkyl amine bis(phenolate) ligand-metal chelate pre-catalyst 11, also referenced as [CH$_3$—CH$_2$—CH$_2$—]—Zr(CH$_2$Ph)$_2$ 11, quantitatively as a colorless crystalline solid.

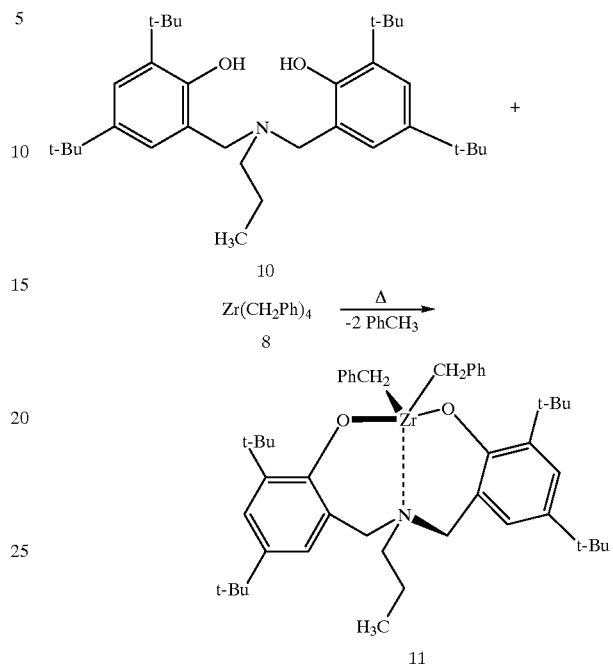

Figure 2:
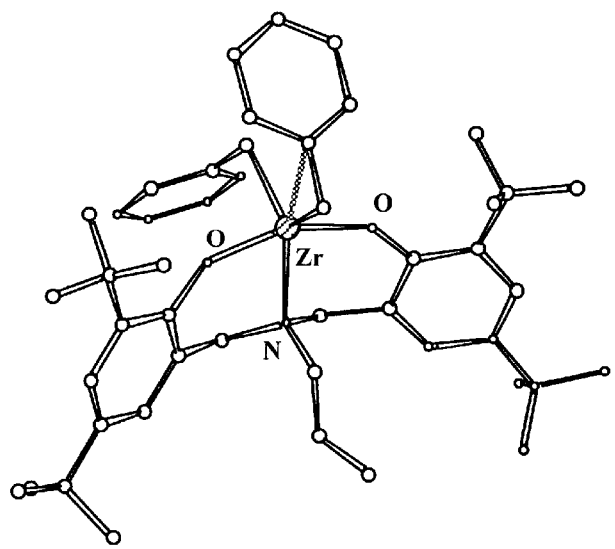
FIG. 2 is an illustration of the X-ray structure of five coordinate dialkyl amine bis(phenolate) ligand-metal chelate pre-catalyst [CH$_3$—CH$_2$—CH$_2$—]—Zr(CH$_2$Ph)$_2$ 11.

Spectroscopic data of ligand-metal pre-catalyst 11 are consistent with a single stereoisomer featuring symmetrically related phenolate rings, two different benzyl groups, and an AX spin system for the two benzylic methylene groups. This points to another rigid chelate of C$_s$ symmetry on the NMR time scale, with the benzyl groups in a non-trans geometry, as required for alpha-olefin polymerization catalysts, and the phenolate groups in a trans geometry. The crystallographic (X-ray) structure of pre-catalyst 11 shown in FIG. 2, supports the spectroscopic data, and indicates a structure featuring a mononuclear zirconium chelate having a pseudo trigonal bi-pyrimidal (TBP) geometry, with axial O atoms and equatorial N, C, C atoms.

In addition to serving as another example of a specific form of amine bis(phenolate) general ligand precursor 6, ligand precursor [CH$_3$—CH$_2$—CH$_2$—] 10 was synthesized for the purpose of synthesizing the five coordinate dialkyl amine bis(phenolate) ligand-metal chelate pre-catalyst, [CH$_3$—CH$_2$—CH$_2$—]—Zr(CH$_2$Ph)$_2$ 11, in order to further understand and measure the influence of the 'extra' heteroatom, in donor group (R$_n$Y—T), in the six coordinate dialkyl amine bis(phenolate) ligand-metal chelate pre-catalyst, [(CH$_3$)$_2$N—CH$_2$—CH$_2$—]—Zr(CH$_2$Ph)$_2$ 9, arising from inclusion of (CH$_3$)$_2$N—CH$_2$—CH$_2$— as donor group (R$_n$Y—T) in the amine bis(phenolate) ligand precursor bridging group, —CH$_2$—(R$_n$Y—T)N—CH$_2$—, for polymerization of alpha-olefin monomers.

Synthesis of third exemplary ligand-metal chelate pre-catalyst [2-Pyridine-CH$_2$—]—Zr(CH$_2$Ph)$_2$ 13. For the third exemplary form of chelate pre-catalyst 1, amine bis(2-hydroxyarylmethyl) specific ligand precursor 12, hereinafter referenced as ligand precursor [2-Pyridine-CH$_2$—] 12, is derived from reaction (not shown) of (2-aminomethyl) pyridine, as a specific form of primary amine 3, with formaldehyde 4 and 2,4-di-tert(butyl)phenol, as a specific form of substituted phenols 5A and 5B. Ligand precursor

[2-Pyridine-CH$_2$—] 12 is a specific form of amine bis(2-hydroxyarylmethyl) general ligand precursor 6, where the bridging group, —CH$_2$—(R$_n$Y—T)N—CH$_2$—, includes (R$_n$Y—T) as the donor group (C$_5$H$_4$N)—CH$_2$—, wherein T is unsaturated hydrocarbyl, —CH$_2$—C—, covalently bonded to the N atom of the bridging group and covalently bonded to Y, and, Y is heteroatom N, which along with a single four-carbon R$_n$ substituent form part of a pyridine aromatic ring system, where pyridine is covalently bonded to the —CH$_2$— part of T, via carbon at pyridine position number 2.

Ligand precursor [2-Pyridine-CH$_2$—] 12 reacts cleanly with one equivalent of zirconium tetra(benzyl), Zr(CH$_2$Ph)$_4$ 8, at 65° C. yielding the six coordinate dialkyl amine bis(phenolate) ligand-metal chelate pre-catalyst 13, also referenced as [2-Pyridine-CH$_2$—]—Zr(CH$_2$Ph)$_2$ 13, quantitatively as a yellow crystalline solid.

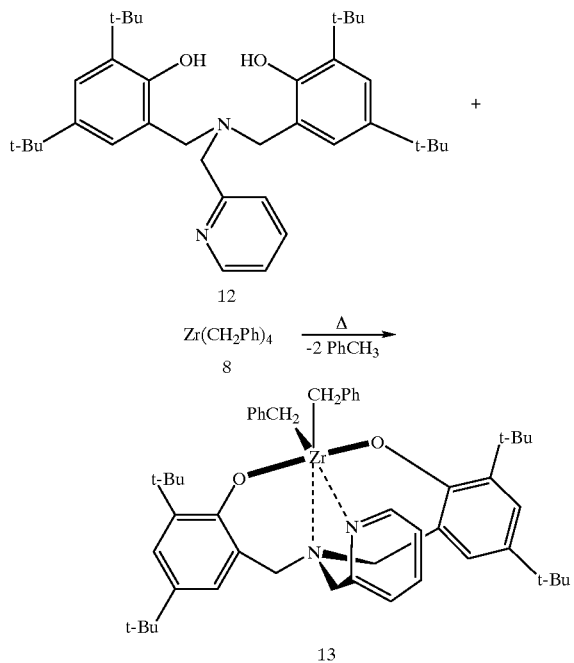

Spectroscopic data of ligand-metal pre-catalyst 13 are consistent with a single stereoisomer featuring symmetrically related phenolate rings, two different benzyl groups, and an AX spin system for the two benzylic methylene groups. This points to a rigid chelate of C$_s$ symmetry on the NMR time scale, with the benzyl groups in a cis geometry, as required for alpha-olefin polymerization catalysts, and the phenolate groups in a trans geometry.

Synthesis of four additional exemplary forms of the amine bis(phenolate) ligand-metal chelate pre-catalyst 1 of the present invention, where, in particular, the metal atom, M, is either the transition metal titanium (Ti), or, the transition metal zirconium (Zr), are described herein.

Synthesis of fourth exemplar ligand-metal chelate pre-catalyst, [(CH$_3$)$_2$N—CH$_2$—]—Ti(CH$_2$Ph)$_2$ 14. For the fourth exemplary form of chelate pre-catalyst 1, ligand precursor [(CH$_3$)$_2$N—CH$_2$—CH$_2$—] 7 reacts with titanium tetra(isopropoxide) at room temperature (25° C.) in diethylether as a solvent. After evaporation of the volatiles, the product is further reacted with two equivalents of trimethylsilyl chloride in methylene chloride at room temperature. After stirring the mixture for two hours, the solvents are evaporated and the product is treated with two equivalents of benzyl magnesium chloride. After an additional two hours, the magnesium chloride is filtered, the solvent is evaporated and the crude product, ligand-metal chelate pre-catalyst 14, also referenced as [(CH$_3$)$_2$N—CH$_2$—CH$_2$—]—Ti(CH$_2$Ph)$_2$ 14, is crystallized from pentane. Ligand-metal chelate pre-catalyst 14 is an exemplary form of chelate catalyst 1, wherein, R$^1$=R$^3$=R$^8$=R$^6$=t-Bu, R$^2$=R$^4$=R$^4$=R$^7$=R$^5$=H, X$^1$=X$^2$=CH$_2$Ph, M=Ti, T=CH$_2$CH$_2$, and, RnY=(CH$_3$)$_2$N.

Synthesis of fifth exemplary ligand-metal chelate pre-catalyst, [(CH$_3$)O—CH$_2$—CH$_2$—]—Ti(CH$_2$Ph)$_2$ 15. The fifth exemplary form of chelate pre-catalyst 1, ligand-metal chelate pre-catalyst 15, also referenced as [(CH$_3$)O—CH$_2$—CH$_2$—]—Ti(CH$_2$Ph)$_2$ 15, synthesized according to a procedure analogous to that used for synthesizing fourth exemplary ligand-metal chelate pre-catalyst 14, from a different ligand precursor which is derived from 2-methoxyethylamine rather than N,N-dimethylethylenediamine. Ligand-metal chelate catalyst 15 is an exemplary form of chelate catalyst 1, wherein, R$^1$=R$^3$=R$^8$=R$^6$=t-Bu, R$^2$=R$^4$=R$^7$=R$^5$=H, X$^1$=X$^2$=CH$_2$Ph, M=Ti, T=CH$_2$CH$_2$, and , RnY=CH$_3$O.

Synthesis of sixth exemplary ligand-metal chelate pre-catalyst, [(CH$_3$CH$_2$)$_2$N—CH$_2$—CH$_2$—]—Zr(CH$_2$Ph)$_2$ 16. The sixth exemplary form of chelate catalyst 1, ligand-metal chelate pre-catalyst 16, also referenced as [(CH$_3$CH$_2$)$_2$N—CH$_2$—CH$_2$—]—Zr(CH$_2$Ph)$_2$ 16, is synthesized according to a procedure analogous to that used for synthesizing first exemplary ligand-metal chelate pre-catalyst 9, from a different ligand precursor which is derived from N,N-diethylethylenediamine rather than N,N-dimethylethylenediamine. Ligand-metal chelate pre-catalyst 16 is an exemplary form of chelate catalyst 1, wherein, R$^1$=R$^3$=R$^8$=R$^6$=t-Bu, R$^2$=R$^4$=R$^7$=R$^5$=H, X$^1$=X$^2$=CH$_2$Ph, M=Zr, T=CH$_2$CH$_2$, and, RnY=(CH$_3$CH$_2$)$_2$N.

Synthesis of seventh exemplary ligand-metal chelate pre-catalyst, [2-Pyridine-CH$_2$—CH$_2$—]—Zr(CH$_2$Ph)$_2$ 17. The seventh exemplary form of chelate pre-catalyst 1, ligand-metal chelate pre-catalyst 17, also referenced as [2-Pyridine-CH$_2$—CH$_2$—]—Zr(CH$_2$Ph)$_2$ 17, is synthesized according to a procedure analogous to that used for synthesizing first exemplary ligand-metal chelate pre-catalyst 9, from a different ligand precursor which is derived from 2-(2-aminoethyl)pyridine rather than N,N-dimethylethylenediamine. Ligand-metal chelate pre-catalyst 17 is an exemplary form of chelate catalyst 1, wherein, R$^1$=R$^3$=R$^8$=R$^6$=t-Bu, R$^2$=R$^4$=R=R$^7$=R$^5$=H, X$^1$=CH$_2$Ph, M=Zr, T=CH$_2$CH$_2$, and, RnY=(C$_5$H$_4$N).

Method for polymerization of alpha-olefin monomers. The method for polymerization of alpha-olefin monomers according to the present invention is herein generally described with respect to using any specific form of the amine bis(phenolate) ligand-metal chelate pre-catalyst 1 or 2, including the seven exemplary specific forms of pre-catalyst 1 as described above, namely, dialkyl amine bis(phenolate) ligand-metal chelate pre-catalyst [(CH$_3$)$_2$N—CH$_2$—CH$_2$—]—Zr(CH$_2$Ph)$_2$ 9, dialkyl amine bis(phenolate) ligand-metal chelate pre-catalyst [CH$_3$—CH$_2$—CH$_2$—]—Zr(CH$_2$Ph)$_2$ 11, dialkyl amine bis(phenolate) ligand-metal chelate pre-catalyst [2-Pyridine-CH$_2$—]—Zr(CH$_2$Ph)$_2$ 13, dialkyl amine bis(phenolate) ligand-metal chelate pre-catalyst [(CH$_3$)$_2$N—CH$_2$—CH$_2$—]—Ti(CH$_2$Ph)$_2$ 14, dialkyl amine bis(phenolate) ligand-metal chelate pre-catalyst [(CH$_3$)O—CH$_2$—CH$_2$—]—Ti (CH$_2$Ph)$_2$ 15, dialkyl amine bis(phenolate) ligand-metal chelate pre-catalyst [(CH$_3$CH$_2$)$_2$N—CH$_2$—CH$_2$—]—Zr(CH$_2$Ph)$_2$ 16, or, dialkyl amine bis(phenolate) ligand-metal chelate pre-catalyst [2-Pyridine-CH$_2$—CH$_2$—]—Zr(CH$_2$Ph)$_2$ 17, respectively.

Novel aspects and features of implementing the method of the present invention for polymerization of an exemplary specific alpha-olefin, 1-hexene, using each of the first three exemplary forms of the amine bis(phenolate) ligand-metal chelate pre-catalyst 9, 11, or 13, for forming poly(1-hexene) product, are provided below, following the description of the method. Details of these polymerization reactions, including related empirical data thereof, are provided below, in Examples 7 and 8, 9, and 10, respectively.

As previously stated above, the accepted parameter for defining polymer molecular weight distribution is the polydispersity index (PDI), which is the weight average molecular weight, M$_w$, divided by the number average molecular weight, M$_n$, or, M$_w$/M$_n$. Depending upon the actual application, in general, preferably, a catalytic polymerization system features 'living' polymerization in which the rate of initiation is higher than the rate of propagation, involving a single catalytic active site, and the rate of termination reactions is negligible relative to propagation, thus, leading to a PDI of close to 1.

Additional novel aspects and features of implementing the method of the present invention for polymerization of alpha-olefin monomers, relating to the categories of: (1) living polymerization performed at or above room temperature, living polymerization performed at room temperature featuring production of exceptionally high molecular weight alpha-olefin polymers, living polymerization along with achieving block co-polymerization of alpha-olefin monomers performed at room temperature, (2) polymerizing a wide variety of alpha-olefin monomers, such as ethylene, propylene, 1-pentene, 1-hexene, 1-octene, 1,5-hexadiene, and, higher alpha-olefin monomers, and, (3) producing polymers and oligomers having a wide range of molecular weights, are also provided below, following the description of the method, in the form of briefly described examples.

The method for catalytic polymerization of alpha-olefin monomers, according to the present invention, described herein, is generally applicable to any type and size chemical reactor and/or chemical process. In particular, the following steps of the method of the present invention can be implemented by using a chemical reactor selected from the group consisting of a continuous flow chemical reactor, a batch chemical reactor, and, a plug-flow chemical reactor, where the size of the chemical reactor is selected from the group consisting of a micro-scale laboratory chemical reactor, a product/process development scale chemical reactor, and, a large scale commercial chemical reactor. Additionally, the following steps of the method of the present invention can be implemented as part of a chemical process selected from the group consisting of a continuous flow chemical process, a batch chemical process, a plug-flow chemical process, and, a combination chemical process featuring a combination of these chemical processes, where the size of the chemical process is selected from the group consisting of a micro-scale laboratory chemical process, a product/process development scale chemical process, and, a large scale commercial chemical process.

In Step (a) of the method for catalytic polymerization of an alpha-olefin monomer, there is providing a particular form of previously described amine bis(phenolate) ligand-metal chelate pre-catalyst 1 or 2.

In Step (b), there is preparing a first chemical entity featuring the particular form of amine bis(phenolate) pre-catalyst 1 or 2 of Step (a) for use in catalytic polymerization of the alpha-olefin monomer.

Preferably, there is mixing a quantity of the particular form of pre-catalyst 1 or 2 with an organic solvent. Any non-protic organic solvent may be used which is capable of suspending or dissolving, without decomposing, pre-catalyst 1 or 2. More preferably, the organic solvent is the liquid form of the alpha-olefin monomer to be polymerized, for example, an organic solvent selected from the group consisting of ethylene (liquid phase), propylene (liquid phase), 1-pentene, 1-hexene, 1-octene, 1,5-hexadiene, and, a higher alpha-olefin monomer.

Alternatively, the organic solvent is the liquid form of the alpha-olefin monomer to be polymerized, for example, an organic solvent selected from the group consisting of ethylene (liquid phase), propylene (liquid phase), 1-pentene, 1-hexene, 1-octene, 1,5-hexadiene, and, a higher alpha-olefin monomer, mixed with at least one additional organic solvent not including the alpha-olefin monomer to be polymerized, for example, at least one additional organic solvent selected from the group consisting of pentane, heptane, toluene, methylene chloride, and, chlorobenzene. The at least one additional organic solvent not including the alpha-olefin monomer can function as an inert diluent in the catalytic polymerization reaction system for the catalytic polymerization of the alpha-olefin monomer. Alternatively, the organic solvent is at least one organic solvent not including the alpha-olefin monomer to be polymerized, for example, at least one organic solvent selected from the group consisting of pentane, heptane, toluene, methylene chloride, and, chlorobenzene.

Alternatively, there is preparing the first chemical entity featuring the particular form of amine bis(phenolate) pre-catalyst 1 or 2 as is, without suspending or dissolving pre-catalyst 1 or 2 in a solvent prior to subsequent Step (e), described below, of forming a catalytic polymerization reaction system for catalytic polymerization of the alpha-olefin monomer. Ordinarily, a suitable co-catalyst is required for activating pre-catalyst 1 or 2 for effecting catalytic polymerization of the alpha-olefin monomer, however, there may exist particular forms of pre-catalyst 1 or 2, which can effect catalytic polymerization of the alpha-olefin monomer without being activated by a co-catalyst. Thus, in such catalytic polymerization systems, pre-catalyst 1 or 2 effectively functions as a 'stand-alone' catalyst, whereby there is no need for performing following Steps (c) and (d), and the method for catalytic polymerization of the alpha-olefin monomer continues with the alternative embodiment of Step (e), described below, immediately following description of the preferred embodiment of Step (e).

Optionally, Step (b) further includes exposing any of the above described preferred or alternative forms of the first chemical entity featuring the particular form of amine bis(phenolate) pre-catalyst 1 or 2, to the surface of at least one solid support or solid substrate such as silica, alumina, magnesia, or, a combination thereof, for preparing an adsorbed state of the first chemical entity of pre-catalyst 1 or 2.

In Step (c), there is providing a co-catalyst suitable for activating particular form of amine bis(phenolate) pre-catalyst 1 or 2, for use in catalytic polymerization of the alpha-olefin monomer. The co-catalyst is selected from the group consisting of, but not limited to, for example, a boron Lewis acid such as tris(pentafluorophenyl)boron, B(C$_6$F$_5$)$_3$, a boron salt such as N,N'-dimethyl anilinium tetrakis(pentafluoro-phenyl)borate, [Ph(CH$_3$)$_2$NH][B(C$_6$F$_5$)$_4$], and, an aluminum compound such as methylaluminoxane (MAO).

In Step (d), there is preparing a second chemical entity featuring the provided co-catalyst of Step (c) for use in catalytic polymerization of the alpha-olefin monomer.

Preferably, there is mixing a quantity of the provided co-catalyst, required for activating pre-catalyst 1 or 2, with an organic solvent. Any non-protic organic solvent may be used which is capable of suspending or dissolving, without decomposing, the provided co-catalyst. More preferably, the organic solvent is the liquid form of the alpha-olefin monomer to be polymerized, for example, an organic solvent selected from the group consisting of ethylene (liquid phase), propylene (liquid phase), 1-pentene, 1-hexene, 1-octene, 1,5-hexadiene, and, a higher alpha-olefin monomer.

Alternatively, the organic solvent is the liquid form of the alpha-olefin monomer to be polymerized, for example, an organic solvent selected from the group consisting of ethylene (liquid phase), propylene (liquid phase), 1-pentene, 1-hexene, 1-octene, 1,5-hexadiene, and, a higher alpha-olefin monomer, mixed with at least one additional organic solvent not including the alpha-olefin monomer to be polymerized, for example, at least one additional organic solvent selected from the group consisting of pentane, heptane, toluene, methylene chloride, and, chlorobenzene. The at least one additional organic solvent not including the alpha-olefin monomer can function as an inert diluent in the catalytic polymerization reaction system for the catalytic polymerization of the alpha-olefin monomer. Alternatively, the organic solvent is at least one organic solvent not including the alpha-olefin monomer to be polymerized, for example, at least one organic solvent selected from the group consisting of pentane, heptane, toluene, methylene chloride, and, chlorobenzene.

Alternatively, there is preparing the second chemical entity featuring the provided co-catalyst as is, without suspending or dissolving the provided co-catalyst in a solvent prior to subsequent preferred embodiment of Step (e), described below, of forming a catalytic polymerization reaction system for catalytic polymerization of the alpha-olefin monomer.

Optionally, Step (d) further includes exposing any of the above described preferred or alternative forms of the second chemical entity featuring the provided co-catalyst, to the surface of at least one solid support or solid substrate such as silica, alumina, magnesia, or, a combination thereof, for preparing an adsorbed state of the second chemical entity of the provided co-catalyst.

With regard to above Step (b) and Step (d), the specific solvent or solvents used for suspending or dissolving amine bis(phenolate) pre-catalyst 1 or 2, and/or for suspending or dissolving the provided co-catalyst, depends upon the desired poly(alpha-olefin) product distribution, especially with respect to formation of different homo-polymers and co-polymers, each having a different degree of alpha-olefin monomer incorporation. Typically, when the alpha-olefin monomer to be polymerized is liquid phase, at least one of the solvents used for suspending or dissolving amine bis (phenolate) pre-catalyst 1 or 2 and/or the provided co-catalyst is the alpha-olefin monomer targeted as the desired poly(alpha-olefin) product.

Molecular weight distribution, measured as PDI, of the product formed is typically affected by the concentration of the alpha-olefin monomer to be polymerized in a solvent, wherein, there is optionally included at least one of the above listed inert diluents, such as pentane, heptane, toluene, methylene chloride, and chlorobenzene. For example, when the alpha-olefin polymerization is conducted in neat 1-hexene, a temperature rise may occur, due to exothermic reaction, generally resulting in a relatively broad polymer molecular weight distribution, leading to a relatively high PDI value. When the same alpha-olefin polymerization is conducted under similar conditions, but using dilute solution of the target 1-hexene and inert diluent such as heptane, reaction temperature rise is milder, and polymer molecular weight distribution is narrower, yielding a lower PDI value.

In the preferred embodiment of Step (e), there is forming a catalytic polymerization reaction for catalytic polymerization of the alpha-olefin monomer by mixing (i) the first chemical entity featuring the particular form of amine bis (phenolate) pre-catalyst 1 or 2 of Step (b), with (ii) the second chemical entity of the provided co-catalyst of Step (d), with (iii) the alpha-olefin monomer which is to be polymerized. Alternative Step (e), wherein pre-catalyst 1 or 2 effectively functions as a 'stand-alone' catalyst for the catalytic polymerization of the alpha-olefin monomer, is described below, immediately following description of the preferred embodiment of Step (e).

In the preferred embodiment of Step (e), preferably, there are two categories, category (A) and category (B), for forming the catalytic polymerization reaction, relating to the mixing of (i) the first chemical entity, with (ii) the second chemical entity, with (iii) the alpha-olefin monomer, according to the presence (category(A)) or absence (category (B)), respectively, of the alpha-olefin monomer which is to be polymerized, in at least one of the first and second chemical entities. In addition to the presence or absence of the alpha-olefin monomer to be polymerized, in each alternative procedure of category (A) and category (B), there is mixing the first chemical entity in a state selected from the group consisting of a non-adsorbed state of the first chemical entity and an adsorbed state of the first chemical entity, with the second chemical entity in a state selected from the group consisting of a non-adsorbed state of the second chemical entity and an adsorbed state of the second chemical entity.

In category (A), wherein the alpha-olefin monomer to be polymerized is present in at least one of the chemical entities selected from the group consisting of the first chemical entity featuring pre-catalyst 1 or 2, and the second chemical entity featuring the provided co-catalyst, there is need for only mixing the first chemical entity featuring pre-catalyst 1 or 2 with the second chemical entity featuring the selected co-catalyst. Accordingly, in category (A), there is no need for separately adding or mixing in the alpha-olefin monomer to be polymerized with the mixture of the first chemical entity and the second chemical entity.

Category (A) for forming the catalytic polymerization reaction includes the following five alternative procedures for mixing the first chemical entity featuring pre-catalyst 1 or 2 with the second chemical entity featuring the provided co-catalyst: (1) mixing the first chemical entity featuring pre-catalyst 1 or 2 suspended or dissolved in the alpha-olefin monomer, in a non-adsorbed state or in an adsorbed state, with the second chemical entity featuring the provided co-catalyst suspended or dissolved in the alpha-olefin monomer, in a non-adsorbed state or in an adsorbed state, (2) mixing the first chemical entity featuring pre-catalyst 1 or 2 suspended or dissolved in the alpha-olefin monomer, in a non-adsorbed state or in an adsorbed state, with the second chemical entity featuring the provided co-catalyst suspended or dissolved in an organic solvent not including the alpha-olefin monomer, in a non-adsorbed state or in an adsorbed state, (3) mixing the first chemical entity featuring pre-catalyst 1 or 2 suspended or dissolved in an organic solvent not including the alpha-olefin monomer, in a non-adsorbed state or in an adsorbed state, with the second chemical entity featuring the provided co-catalyst suspended or dissolved in the alpha-olefin monomer, in a non-adsorbed state or in an adsorbed state, (4) mixing the first chemical entity, featuring pre-catalyst 1 or 2 suspended or dissolved in the alpha-olefin monomer, in a non-adsorbed state or in an adsorbed state, with the second chemical entity featuring the provided co-catalyst as is, not suspended or dissolved in an organic solvent, in a non-adsorbed state or in an adsorbed state, and (5) mixing the first chemical entity featuring pre-catalyst 1 or 2 as is, not suspended or dissolved in an organic solvent, in a non-adsorbed state or in an adsorbed state, with the second chemical entity featuring the provided co-catalyst suspended or dissolved in the alpha-olefin monomer, in a non-adsorbed state or in an adsorbed state.

In category (B), wherein the alpha-olefin monomer to be polymerized is absent from all of the chemical entities selected from the group consisting of the first chemical entity featuring pre-catalyst 1 or 2, and the second chemical entity featuring the provided co-catalyst, there is mixing the first chemical entity featuring pre-catalyst 1 or 2 with the second chemical entity featuring the provided co-catalyst, followed by mixing with the desired or targeted alpha-olefin monomer to be polymerized.

Category (B) for forming the catalytic polymerization reaction includes the following four alternative procedures for mixing the first chemical entity featuring pre-catalyst 1 or 2 with the second chemical entity featuring the provided co-catalyst, followed by mixing with the alpha-olefin monomer: (1) mixing the first chemical entity featuring pre-catalyst 1 or 2 suspended or dissolved in an organic solvent not including the alpha-olefin monomer, in a non-adsorbed state or in an adsorbed state, with the second chemical entity featuring the provided co-catalyst suspended or dissolved in an organic solvent not including the alpha-olefin monomer, in a non-adsorbed state or in an adsorbed state, followed by mixing with the alpha-olefin monomer, (2) mixing the first chemical entity featuring pre-catalyst 1 or 2 suspended or dissolved in an organic solvent not including the alpha-olefin monomer, in a non-adsorbed state or in an adsorbed state, with the second chemical entity featuring the provided co-catalyst as is, not suspended or dissolved in an organic solvent, in a non-adsorbed state or in an adsorbed state, followed by mixing with the alpha-olefin monomer, (3) mixing the first chemical entity featuring pre-catalyst 1 or 2 as is, not suspended or dissolved in an organic solvent, in a non-adsorbed state or in an adsorbed state, with the second chemical entity featuring the provided co-catalyst suspended or dissolved in an organic solvent not including the alpha-olefin monomer, in a non-adsorbed state or in an adsorbed state, followed by mixing with the alpha-olefin monomer, and (4) mixing the first chemical entity featuring pre-catalyst 1 or 2 as is, not suspended or dissolved in an organic solvent, in a non-adsorbed state or in an adsorbed state, with the second chemical entity featuring the provided co-catalyst as is, not suspended or dissolved in an organic solvent, in a non-adsorbed state or in an adsorbed state, followed by mixing with the alpha-olefin monomer.

In category (B) for forming the catalytic polymerization reaction, according to the above described four alternative procedures, the alpha-olefin monomer is in either a liquid phase or a gas phase for mixing with the initially formed liquid phase mixture or solid phase mixture of the first chemical entity featuring pre-catalyst 1 or 2 and the second chemical entity featuring the provided co-catalyst. Accordingly, liquid phase alpha-olefin monomer is added to the initially formed liquid phase mixture or solid phase mixture of the first chemical entity featuring pre-catalyst 1 or 2 and the second chemical entity featuring the provided co-catalyst. Alternatively, gas phase alpha-olefin monomer is bubbled into and/or through the initially formed liquid phase mixture or solid phase mixture of the first chemical entity featuring pre-catalyst 1 or 2 and the second chemical entity featuring the provided co-catalyst.

Independent of the actual category, order, sequence, or, detailed procedure, of handling the chemical entities, for implementing the preferred embodiment of Step (e), for forming a catalytic polymerization reaction for catalytic polymerization of the alpha-olefin monomer, by mixing (i) the first chemical entity featuring the particular form of amine bis(phenolate) pre-catalyst 1 or 2 of Step (b), with (ii) the second chemical entity of the provided co-catalyst of Step (d), with (iii) the alpha-olefin monomer which is to be polymerized, completion of the preferred embodiment of Step (e) results in forming the catalytic polymerization reaction for catalytic polymerization of the alpha-olefin monomer, including (i) the first chemical entity featuring the particular form of amine bis(phenolate) pre-catalyst 1 or 2 of Step (b), in a non-adsorbed state or in an adsorbed state, (ii) the second chemical entity featuring the provided co-catalyst of Step (d), in a non-adsorbed state or in an adsorbed state, and (iii) the alpha-olefin monomer which is to be polymerized.

Moreover, independent of the actual category, order, sequence, or, detailed procedure, of handling the chemical entities, for implementing the preferred embodiment of Step (e), for forming a catalytic polymerization reaction for catalytic polymerization of the alpha-olefin monomer, once in contact, physicochemical interaction of pre-catalyst 1 or 2 and the provided co-catalyst enables activation of pre-catalyst 1 or 2, and the combination of pre-catalyst 1 or 2 and the provided co-catalyst results in formation of a combined or complex catalyst for effecting the catalytic polymerization of the alpha-olefin monomer, for producing at least one type of poly(alpha-olefin) product.

In practice, implementation of the method for catalytic polymerization of an alpha-olefin monomer, according to the present invention, typically involves performing above described preferred embodiment of Step (e), of forming a catalytic polymerization reaction for catalytic polymerization of the alpha-olefin monomer by mixing (i) the first chemical entity featuring the particular form of amine bis (phenolate) pre-catalyst 1 or 2 of Step (b), with (ii) the second chemical entity of the provided co-catalyst of Step (d), with (iii) the alpha-olefin monomer which is to be polymerized, according to any particular procedure selected from category (A) or category (B).

In principle, the complex chemical entity formed as a result of mixing the first chemical entity featuring pre-catalyst 1 or 2 absent of the alpha-olefin monomer, in a non-adsorbed state or in an adsorbed state, with the second chemical entity featuring the provided co-catalyst also absent of the alpha-olefin monomer, in a non-adsorbed state or in an adsorbed state, can be isolated and held as is, short term or long term, according to stability of such a complex chemical entity, without immediately exposing the complex chemical entity to an alpha-olefin monomer for forming a catalytic polymerization reaction for catalytic polymerization of an alpha-olefin monomer. In this case, the complex chemical entity formed by activating pre-catalyst 1 or 2 with the provided co-catalyst, in the absence of alpha-olefin monomer, is effectively considered an 'active' catalyst for catalytic polymerization of an alpha-olefin monomer, such that, by separately adding an alpha-olefin monomer to the complex chemical entity, there is forming a catalytic polymerization reaction for catalytic polymerization of the alpha-olefin monomer, in accordance with previously described category (B) of the preferred embodiment of Step (e).

According to previously described Step (b) there may exist particular forms of pre-catalyst 1 or 2, which can effect catalytic polymerization of the alpha-olefin monomer without being activated by a co-catalyst, whereby following preparation of the first chemical entity featuring the particular form of amine bis(phenolate) pre-catalyst 1 or 2, according to previously described Step (b), there is no need for preparing the second chemical entity featuring the provided co-catalyst, according to previously described Steps (c) and (d). Thus, in the alternative embodiment of Step (e), there is forming a catalytic polymerization reaction for catalytic polymerization of the alpha-olefin monomer by mixing (i) the first chemical entity featuring the particular form of amine bis(phenolate) precatalyst 1 or 2, suspended or dissolved in liquid phase, or, as is, in liquid phase or solid phase, in a non-adsorbed state or in an adsorbed state, without including the alpha-olefin monomer, according to previously described Step (b), with (ii) the alpha-olefin monomer which is to be polymerized.

In the alternative embodiment of Step (e), preferably, liquid phase alpha-olefin monomer is added to the initially prepared liquid phase or solid phase of the first chemical entity featuring precatalyst 1 or 2 in a non-adsorbed state or in an adsorbed state.

Alternatively, gas phase alpha-olefin monomer is bubbled into and/or through the initially prepared liquid phase or solid phase of the first chemical entity featuring precatalyst 1 or 2 in a non-adsorbed state or in an adsorbed state.

Independent of the actual category, order, sequence, or, detailed procedure, of handling the chemical entities, for implementing the alternative embodiment of Step (e), for forming a catalytic polymerization reaction for catalytic polymerization of the alpha-olefin monomer, by mixing (i) the first chemical entity featuring the particular form of amine bis(phenolate) precatalyst 1 or 2, suspended or dissolved in liquid phase, or, as is, in liquid phase or solid phase, in a non-adsorbed state or in an adsorbed state, according to previously described Step (b), with (ii) the alpha-olefin monomer which is to be polymerized, completion of the alternative embodiment of Step (e) results in forming the catalytic polymerization reaction system for catalytic polymerization of the alpha-olefin monomer, including (i) the first chemical entity featuring the particular form of amine bis(phenolate) precatalyst 1 or 2 of Step (b), in a non-adsorbed state or in an adsorbed state, whereby precatalyst 1 or 2 effectively functions as a 'stand-alone' catalyst, and (ii) the alpha-olefin monomer which is to be polymerized.

In general, conditions for performing Step (a) through preferred Step (e) or alternative Step (e) include a pressure range of from about 0.1 bar to about 50 bar, and, a temperature range of from about −78° C. to about 150° C., with exclusion of moisture and oxygen, in order to prevent hydrolysis or oxidation of either the pre-catalyst or the co-catalyst. Exclusion of moisture and oxygen prior to introducing the first and second chemical entities into the chemical reactor is performed by a procedure selected from the group consisting of (i) using an inert atmosphere, (ii) evacuating the chemical reactor, (iii) washing the chemical reactor using the alpha-olefin monomer to be polymerized and/or using one of the above listed inert solvents, (iv) heating the chemical reactor, and, (v) a combination thereof. Exclusion of moisture and oxygen is preferably accomplished by using an inert atmosphere, such as an inert atmosphere selected from the group consisting of nitrogen, helium, argon, and mixtures thereof. Preferably, conditions for performing Step (a) through preferred Step (e) or alternative Step (e) include a pressure range of from about 1 bar to about 5.5 bar, a temperature range of from about 20° C. to about 30° C., and in particular, at room temperature of about 25° C., with exclusion of moisture and oxygen as described above.

In Step (f), there is allowing the catalytic polymerization reaction to progress.

Typically, while the catalytic polymerization reaction progresses, there is stirring the catalytic polymerization reaction. In general, there is stirring the catalytic polymerization reaction for a duration in the range of from about 5 seconds to about 100 hours. Preferably, there is stirring the catalytic polymerization reaction for a duration in the range of from about 5 seconds to about 30 hours.

The catalytic polymerization progresses and is performed at different temperatures. Starting from polymerization reaction initiation, and including duration of stirring of the reaction system, exothermic heat may be released from the reaction system, accompanied by possible color change of the catalytic polymerization reaction system. External cooling, for example, down to about 0° C., may be used for slowing down the catalytic polymerization. Heating, for example, to reflux temperature, may be used for speeding up the catalytic polymerization reaction.

Additionally, in Step (f), optionally, there is adding to the catalytic polymerization reaction at least one other type and quantity of a chemical reagent for improving the polymerization reaction. For example, hydrogen gas is sometimes added to the catalytic polymerization reaction for improving control of molecular weight of the resulting poly(alpha-olefin) products.

In Step (g), there is terminating/termination of the catalytic polymerization reaction.

In general, there is either terminating the catalytic polymerization reaction by involving means initially 'external' to the catalytic polymerization reaction, such as by (i) adding an external quencher, such as a protic solvent, to the catalytic polymerization reaction, (ii) removing remaining alpha-olefin monomer from the catalytic polymerization reaction, and, (iii) a combination thereof. Additionally, or, alternatively, there is termination of the catalytic polymerization reaction by means 'internal' to the catalytic polymerization reaction, such as by (i) complete consumption of the alpha-olefin monomer, (ii) deactivation of the catalyst formed during the progression of the catalytic polymerization reaction, and, (iii) a combination thereof.

Regarding termination of the catalytic polymerization reaction by internal means (ii), with respect to the catalytic polymerization reaction formed according to the previously described preferred embodiment of Step (e), above, there is deactivation of the catalyst formed during the progression of the polymerization reaction, wherein the formed catalyst features a complex of the first chemical entity featuring the particular form of amine bis(phenolate) precatalyst 1 or 2 of Step (b), mixed with the second chemical entity of the provided co-catalyst of Step (d). With respect to the catalytic polymerization reaction formed according to the previously described alternative embodiment of Step (e), above, there is deactivation of the catalyst formed during the progression of the catalytic polymerization reaction, wherein the formed catalyst features a form of the first chemical entity, featuring the particular form of amine bis(phenolate) precatalyst 1 or 2 of Step (b), without the presence of the second chemical entity of the provided co-catalyst of Step (d).

In Step (h), there is isolating at least one polymer product formed by the catalytic polymerization reaction.

There is isolating at least one, typically, only one, principal or most abundant poly(alpha-olefin), polymer product formed by the catalytic polymerization reaction by using the following procedure. Excess precatalyst 1 or 2 and/or the provided co-catalyst, if present, may be hydrolyzed. Isolation of the polymer product from the solvent and/or remaining alpha-olefin monomer in solution depends upon the solubility of the polymer product. In the case of an insoluble polymer product, for example, polyethylene, the isolation procedure includes filtration and drying, whereas in the case of a soluble polymer product, volatile species are removed by distillation and the polymer product is then dried. Impurities, such as decomposition products of precatalyst 1 or 2 and/or the provided co-catalyst, if present, are typically washed away.

In Step (i), there is measuring and analyzing physicochemical properties and characteristics of the at least one polymer product formed by the catalytic polymerization reaction of the alpha-olefin monomer by various techniques, such as melting point, for example, by applying DSC (differential scanning calorimetry), spectroscopy such as NMR, X-ray crystallography, mechanical strength such as elasticity, etc. Structural information and molecular weight information relating to polymer molecular weight distribution via the polydispersity index (PDI), are also determined.

To illustrate the ultra-high catalytic activity exhibited by amine bis(phenolate) ligand-metal chelate pre-catalyst 1 of the present invention for polymerization of alpha-olefin monomers, selected novel aspects and features of polymerization reactions detailed in Examples 7–10, below, are provided herein.

Amine bis(phenolate) ligand-metal chelate pre-catalyst 1 in the first exemplary specific form described above, namely, six coordinate dialkyl amine bis(phenolate) ligand-metal chelate pre-catalyst $[(CH_3)_2N—CH_2—CH_2—]—Zr(CH_2Ph)_2$ 9, is activated by boron Lewis acid co-catalyst, $B(C_6F_5)_3$, in the presence of neat 1-hexene at room temperature under nitrogen gas inert atmosphere, where 1-hexene functions as both the target alpha-olefin monomer to be polymerized and as dissolution solvent for pre-catalyst 9 and for the boron co-catalyst.

Unexpectedly, the ensuing reaction resulted in dramatic generation of exothermic heat, resulting in boiling of the 1-hexene monomer at 64° C., and extremely rapid formation of poly(1-hexene) product. Consumption of the 1-hexene monomer was essentially complete after only about 2 minutes. Average molecular weight of the poly(1-hexene) product was measured as $M_w=12,700$ grams/mole, and the PDI was 6. The relatively broad molecular weight distribution may be caused by the relatively high temperature of the polymerization mixture arising from a relatively high rate of exothermic heat evolved under these reaction conditions.

For this catalytic polymerization reaction, catalytic activity of pre-catalyst 9 was calculated from reaction data as 21,000 (grams poly(1-hexene) produced)/(mmole-pre-cat. hr). This magnitude of catalytic activity of a non-metallocene type pre-catalyst for catalytic polymerization of an alpha-olefin monomer is exceptionally high considering the relatively unfavorable polymerization reaction conditions involving use of a small quantity of a moderately active, non-MAO, boron co-catalyst, and where labile groups in polymerization pre-catalyst 9 are benzyl groups.

When the same pre-catalyst $[(CH_3)_2N—CH_2—CH_2—]—Zr(CH_2Ph)_2$ 9 is activated by the same boron Lewis acid co-catalyst, $B(C_6F_5)_3$, in 1-hexene diluted with heptane diluent, to an extent of heptane: 1-hexene volume ratio of 7:3, at room temperature under nitrogen gas inert atmosphere, a significantly less vigorous polymerization reaction takes place. Catalytic activity calculated from the reaction data in this case is still relatively high at 2000 (grams poly(1-hexene) produced)/(mmole-pre-cat. hr). Compared to catalytic polymerization of 1-hexene monomer using pre-catalyst 9 activated in neat 1-hexene, exothermic heat evolved by the reaction mixture in dilute 1-hexene was significantly milder, resulting in a substantially lower catalytic activity.

Figure 3:
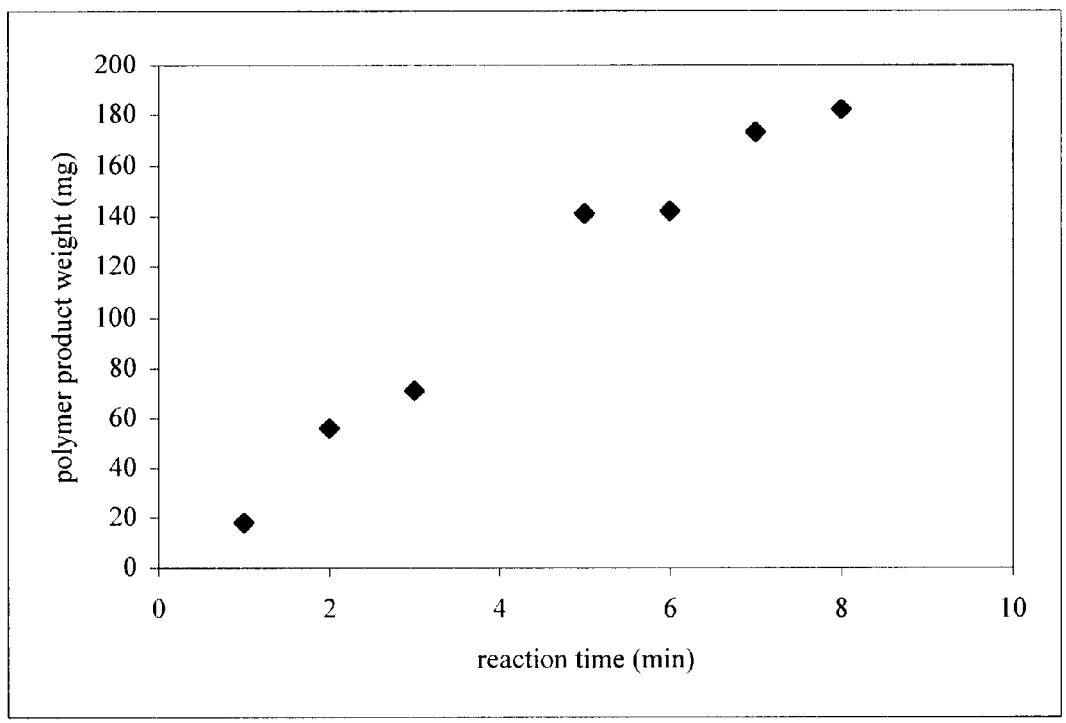
FIG. 3 is an illustration of catalytic activity of amine bis(phenolate) ligand-metal chelate pre-catalyst [(CH$_3$)$_2$N—CH$_2$—CH$_2$—]—Zr(CH$_2$Ph)$_2$ 9 for the polymerization of 1-hexene alpha-olefin monomer in dilute 1-hexene.

In this reaction system, consumption of 1-hexene monomer versus time was measured and found to be linear, as shown in FIG. 3, an illustration of catalytic activity of amine bis(phenolate) ligand-metal chelate pre-catalyst $[(CH_3)_2N—CH_2—CH_2—]—Zr(CH_2Ph)_2$ 9 for the polymerization of 1-hexene alpha-olefin monomer in dilute 1-hexene. The data of FIG. 3 show that this reaction system is active for at least 8 minutes, after which about 80% of the 1-hexene monomer is consumed, under these conditions. The poly(1-hexene) product had a high molecular weight of $M_w=170,000$ grams/mole, with a low PDI of 2.2.

In another example of highly active catalytic polymerization of exemplary alpha-olefin monomer 1-hexene, six coordinate dialkyl amine bis(phenolate) ligand-metal chelate pre-catalyst $[2\text{-Pyridine-}CH_2—]—Zr(CH_2Ph)_2$ 13 is activated by boron Lewis acid co-catalyst, $B(C_6F_5)_3$, in the presence of neat 1-hexene at room temperature under nitrogen gas inert atmosphere, where again 1-hexene functions as both the target alpha-olefin monomer to be polymerized and as dissolution solvent for pre-catalyst 13 and for the boron co-catalyst. Considerable exothermic heat of reaction is evolved, leading to a catalytic activity calculated from the reaction data of about 10,000 (grams poly(1-hexene) produced)/(mmole-pre-cat. hr). Results of high catalytic activity obtained from this catalytic reaction, using pre-catalyst 13, are very similar to those obtained when using pre-catalyst 9, for polymerization of 1-hexene alpha-olefin monomer.

Catalytic activity of amine bis(phenolate) ligand-metal chelate pre-catalyst 1 of the present invention, illustrated in part, by specific forms of six coordinate amine bis(phenolate) ligand-metal chelate, pre-catalyst $[(CH_3)_2N—CH_2—CH_2—]—Zr(CH_2Ph)_2$ 9, and pre-catalyst $[2\text{-Pyridine-}CH_2—]—Zr(CH_2Ph)_2$ 13, operating under the above described reaction conditions, is up to several orders of magnitude higher than catalytic activity of currently used non-metallocene pre-catalysts and related catalytic systems. For example, prior art non-metallocene pre-catalysts and catalytic systems activated by a non-MAO co-catalyst for catalytic polymerization of 1-hexene exhibit relatively lower catalytic activities of about 400, 200, 40, and 10, grams/(mmole-pre-cat. hr), as reported by Kim, K., in *Organometallics* 17, 3161, 1998, disclosed in U.S. Pat. No. 5,889,128, reported by McConville, D. H., in *J. Am. Chem. Soc.* 118, 10008, 1996, and reported by Schaverien, C. J., in *J. Am. Chem. Soc.* 117, 3008, 1995, respectively.

Several additional novel aspects and features of the method of the present invention for polymerization of alpha-olefin monomers, relating to the previously stated categories of: (1) living polymerization performed at or above room temperature, living polymerization performed at room temperature featuring production of exceptionally high molecular weight alpha-olefin polymers, living polymerization along with achieving block co-polymerization of alpha-olefin monomers performed at room temperature, (2) polymerizing a wide variety of alpha-olefin monomers, such as ethylene, propylene, 1-pentene, 1-hexene, 1-octene, 1,5-hexadiene, and, higher alpha-olefin monomers, and, (3) producing polymers and oligomers having a wide range of molecular weights, are described herein below, accompanied by selected highlights of appropriately supporting specific examples.

(a) Living polymerization performed under the very rare conditions of room temperature, characterized by a very narrow polydispersity index (PDI) of close to 1.0.

The above described specific forms of amine bis (phenolate) ligand-metal chelate precatalyst 1 or 2, when activated with a co-catalyst, such as the Lewis acid co-catalyst $B(C_6F_5)_3$, features living polymerization of alpha-olefin monomers, such as 1-hexene. For example, activating pre-catalyst $[(CH_3)_2N—CH_2—CH_2—]—Ti(CH_2Ph)_2$ 14 with approximately one equivalent of $B(C_6F_5)_3$ at room temperature (20–30° C., preferably, 25° C.) under a nitrogen atmosphere, in the presence of 1-hexene, preferably, neat 1-hexene, yields a polymer having a molecular weight of 14,000 grams/mole and having a polydispersity index of 1.18.

(b) Forming a catalyst which remains 'alive' for an exceptionally long period of time, for producing 'in a living fashion' a polymer having exceptionally high molecular weight.

The above described specific forms of amine bis (phenolate) ligand-metal chelate precatalyst 1 or 2, when activated with a co-catalyst, such as the Lewis acid co-catalyst $B(C_6F_5)_3$, features unique living properties of polymerization of alpha-olefin monomers, such as 1-hexene. For example, activating pre-catalyst $[(CH_3)O—CH_2—CH_2—]—Ti(CH_2Ph)_2$ 15 with approximately one equivalent of $B(C_6F_5)_3$ at room temperature (20–30° C., preferably, 25° under a nitrogen atmosphere, in the presence of 1-hexene, preferably, neat 1-hexene, results in a catalyst that remains living for an exceptionally long period of time, on the order of 30 hours, producing a polymer having an exceptionally high molecular weight, of as high as 450,000 grams/mole, in a living fashion (PDI=1.12).

(c) Living polymerization of alpha-olefin monomers performed 'above' room temperature.

The above described specific forms of amine bis (phenolate) ligand-metal chelate precatalyst 1 or 2, when activated with a co-catalyst, such as the Lewis acid co-catalyst $B(C_6F_5)_3$, features living polymerization of alpha-olefin monomers, such as 1-hexene, 'above' room temperature. For example, activating pre-catalyst $[(CH_3)O—CH_2—CH_2—]—Ti(CH_2Ph)_2$ 15 with approximately one equivalent of $B(C_6F_5)_3$, 'above' room temperature, that is, in the temperature range of from about 25° C. to about 50° C., preferably, at 40° C., under a nitrogen atmosphere, in the presence of 1-hexene, preferably, neat 1-hexene, produces a polymer having a PDI of 1.14.

(d) Living polymerization while achieving block co-polymerization of alpha-olefin monomers performed at room temperature.

The above described specific forms of amine bis (phenolate) ligand-metal chelate precatalyst 1 or 2, when activated with a co-catalyst, such as the Lewis acid co-catalyst $B(C_6F_5)_3$, features living polymerization of alpha-olefin monomers, such as 1-hexene, while achieving block co-polymerization of the alpha-olefin monomers, performed at room temperature.

A potentially important industrial application of living polymerization of alpha-olefin monomers is the synthesis of block copolymers. This requires either total or nearly total consumption of the first monomer to produce a narrow PDI fragment before addition of the second monomer, upon which the polymerization process should resume. These requirements are extremely difficult to attain, and therefore it is no surprise that despite the intensive efforts invested in the field of alpha-olefin polymerization, very few reaction systems that induce living polymerization of alpha-olefin monomers are known to be applicable for producing block co-polymers. Moreover, all such prior art polymerization reaction systems operate below room temperature (25° C.).

For example, when pre-catalyst $[(CH_3)O—CH_2—CH_2—]—Ti(CH_2Ph)_2$ 15 is dissolved in an organic solvent, such as chlorobenzene, and about 110 equivalents of 1-hexene are added under a nitrogen atmosphere at room temperature (20–30° C., preferably, 25° C.), there is observed complete consumption of the 1-hexene about 3 hours after activation with co-catalyst $B(C_6F_5)_3$. This observation is evident from the final weight of the polymeric product, being similar to the weight of the monomer employed. At this time of the polymerization reaction, the molecular weight of the polymeric product is found to be $M_n$=9,000 grams/mole (PDI=1.19), in accordance with the 1-hexene employed, polymerized in a living fashion. In order to ascertain the complete consumption of the first monomer, a second monomer, in particular, 1-octene, is added only after about a 1.5 hours delay period. After additional polymerization time of about 2 hours, a block copolymer having a molecular weight of $M_n$=11,600 grams/mole (PDI=1.22) is obtained.

(e) Polymerizing a wide variety of alpha-olefin monomers, such as 1-pentene, 1-hexene, 1-octene 1,5-hexadiene, and the ones of highest industrial significance: propylene and ethylene.

The above described specific forms of amine bis (phenolate) ligand-metal chelate precatalyst 1 or 2, when activated with a co-catalyst, such as an aluminum compound co-catalyst, for example, methylaluminoxane (MAO), are used for catalytic polymerization of alpha-olefin monomers, such as an alpha-olefin monomer selected from the group consisting of ethylene, propylene, 1-pentene, 1-hexene, 1-octene, 1,5-hexadiene, and, a higher alpha-olefin monomer. The method for catalytic polymerization of the liquid-phase monomers, 1-octene, and, 1,5-hexadiene, is similar to that for catalytic polymerization of liquid phase 1-hexene.

In another example, there is polymerization of liquid phase propylene, preferably, liquid phase neat propylene. This is performed by vacuum transferring the propylene into a reactor holding pre-catalyst $[(CH_3)_2N—CH_2—CH_2—]—Zr(CH_2Ph)_2$ 9 and a relatively low number of equivalents, in particular, about 250 equivalents, of solid MAO co-catalyst. In general, this polymerization reaction is implemented by using a number of equivalents in the range of from about 100 equivalents to about 10,000 equivalents, of solid MAO co-catalyst. The reaction mixture is allowed to warm to room temperature (20–30° C., preferably, 25° C.). After about 24 hours, nearly complete consumption of the propylene monomer is observed. The polypropylene obtained is atactic according to $^{13}C$ NMR, and has a high molecular weight of $M_w$=350,000 grams/mole, resulting in a plastic having elastomeric properties. The polymer obtained has a narrow PDI of 2.0, indicating that even under these industrially relevant conditions, a single-site catalyst is operative. Very high turnover numbers of 500,000 mol-propylene/mol-cat are consistent with the formed catalyst being active for a relatively long time.

In another example, there is polymerization of gas phase ethylene. Reaction conditions are variable, including pressure in the range of from about 0.1 bar to about 50 bar, preferably, in the range of from about 1 bar to about 5.5 bar, solvent, such as one of the solvents according to previously described Steps 1 and 2, for example, heptane, toluene, or, chlorobenzene, and, temperature in the range of from about −78° C. to about 150° C., preferably, in the range of from about room temperature (20–30° C., preferably, 25° C.) to about 140° C.

For example, pre-catalyst [(CH$_3$)$_2$N—CH$_2$—CH$_2$—]—Zr(CH$_2$Ph)$_2$ 9 and about 500 equivalents of solid MAO are dissolved in an organic solvent, such as chlorobenzene, along with using about 5.5 bar of gas phase ethylene. In general, this polymerization reaction is implemented by using a number of equivalents in the range of from about 100 equivalents to about 10,000 equivalents, of solid MAO co-catalyst. The pre-catalyst exhibited an activity of 500 (grams polymer produced)/(mmole-pre-cat. hr bar). The polymer obtained is insoluble in all common organic solvents, and has a relatively high melting point of 130° C. as measured by DSC (differential scanning calorimetry). This is consistent with formation of 'high density polyethylene' as expected of a non-branched polymer.

(f) Producing polymers having a wide range of molecular weights as high as 450,000 grams/mole, as well as oligomers with molecular weights of about 1000 grams/mole.

The above described specific forms of amine bis (phenolate) ligand-metal chelate precatalyst 1 or 2, when activated with a co-catalyst, such as the Lewis acid co-catalyst B(C$_6$F$_5$)$_3$, features polymerization of alpha-olefin monomers, such as 1-hexene, for producing polymers having a wide range of molecular weights of as high as 450,000 grams/mole, as well as oligomers with molecular weights of about 1000 grams/mole.

As previously described in (b) above, pre-catalyst [(CH$_3$)O—CH$_2$—CH$_2$—]—Ti(CH$_2$Ph)$_2$ 15 can be used for producing polymers having molecular weights of as high as 450,000 grams/mole. By contrast, using the above described specific forms of amine bis(phenolate) ligand-metal chelate precatalyst 1 or 2, at appropriate reaction conditions, leads to oligomerization. For example, activating pre-catalyst [(CH$_3$CH$_2$)$_2$N—CH$_2$—CH$_2$—]—Zr(CH$_2$Ph)$_2$ 16 with approximately one equivalent of B(C$_6$F$_5$)$_3$ at room temperature (20–30° C., preferably, 25° C.) under a nitrogen atmosphere, in the presence of 1-hexene, preferably, neat 1-hexene, produces oligomers having a molecular weight of 1,100 grams/mole with a PDI of 1.6, resulting from termination processes and reinitiation of a reactive catalyst formed during the polymerization reaction. In this example of oligomerization, the pre-catalyst exhibited an activity of 60 (grams polymer produced)/(mmole-pre-cat. hr).

In another example, pre-catalyst [2-Pyridine-CH$_2$—CH$_2$—]—Zr(CH$_2$Ph)$_2$ 17, used at reaction conditions similar to the immediately preceding example, according to the described method, leads to the pre-catalyst exhibiting a similar activity of 65 (grams polymer produced)/(mmole-pre-cat. hr), but, in contrast, the polymerization produces high molecular weight polymers, for example, having $M_w$=102,000 grams/mole, and PDI=1.7.

Additional objects, advantages, and novel features of the present invention will become apparent to one ordinarily skilled in the art upon examination of the following examples, which are not intended to be limiting. Additionally, each of the various embodiments and aspects of the present invention as delineated herein above and as claimed below finds experimental support in the following examples.

Details of the syntheses and spectroscopic data of the resulting structures of three different specific forms of the amine bis(2-hydroxyarylmethyl) general ligand precursor 6, corresponding to each exemplary form of the bridging group, —CH$_2$—(R$_n$Y—T)N—CH$_2$—, including a different form of the group (R$_n$Y—T), are provided in Examples 1, 2, and 3, respectively, below. Details of the syntheses and, spectroscopic and X-ray data of resulting structures of corresponding exemplary forms of the amine bis(phenolate) ligand-metal chelate pre-catalyst 1 of the present invention are provided in Examples 4, 5, and 6, respectively, below.

Details of catalytic polymerization of an exemplary specific alpha-olefin, 1-hexene, using each of the first three corresponding exemplary specific forms of amine bis (phenolate) ligand-metal chelate catalyst 1, namely, amine bis(phenolate) ligand-metal chelate pre-catalyst 9, 11, or 13, in accordance with the method of the present invention, for forming poly(1-hexene) product, and related empirical data thereof, are herein provided in Examples 7 and 8, 9, and 10, respectively.

Reference numbers of chemical species and structures appearing in the following examples are identical to those assigned in the above descriptions of the preferred embodiments.

EXAMPLE 1

Synthesis of amine bis(2-hydroxyarylmethyl) ligand precursor [(CH$_3$)$_2$N—CH$_2$—CH$_2$—] 7

Amine bis (2-hydroxyarylmethyl) ligand precursor [(CH$_3$)$_2$N—CH$_2$—CH$_2$—] 7 was recently prepared in a multi-step procedure and in relatively low yields by Hirotsu, M. et al., in *Bull. Chem. Soc. Jpn.* 70, 649, 1997, using a modification of a method reported by Hinshaw, C. J. et al., in *Inorg. Chem.* 28, 4483, 1989. The following is a moderate yield, one step procedure, which utilizes commercially available starting materials.

A solution of 2,4-di-tert(butyl)phenol (5 g, 24.2 mmol), N,N-dimethylethylenediamine (1.8 mL, 16.4 mmol), and 36% aqueous formaldehyde (2.5 mL, 33.6 mmol) in methanol (10 mL), was stirred at room temperature for three days. The mixture was cooled in a freezer over night, filtered, and washed thoroughly with ice cold methanol, to give the bis-adduct 7 as a colorless powder (3.7 g, 58.3% yield), which could be further purified by re-crystallization from methanol.

Melting point of 7 was 158° C.

Spectroscopic Data of 7. $^1$H NMR (C$_6$D$_6$, 200 MHz) δ9.86 (s, 2H, OH), 7.50 (d, J=2.3, 2H, Ar), 6.98 (d, J=2.3, 2H, Ar), 3.39 (s, 4H, CH$_2$), 2.19 (m, 2H, CH$_2$), 1.93 (s, 6H N(CH$_3$)$_2$), 1.67 (s, 18H, C(CH$_3$)$_3$), 1.34 (s, 18H, C(CH$_3$)$_3$). $^{13}$C NMR (CDCl$_3$ 151.14 MHz) δ153.3, 140.1, 136.0, 124.8, 123.3, 121.6, 56.6 (ArCH$_2$N), 56.9 (NCH$_2$), 49.0 (NCH$_2$), 44.8 (N(CH$_3$)$_2$), 35 (C—C), 34.0 (C—C), 31.7 (CH3), 29.5 (CH$_3$).

EXAMPLE 2

Synthesis of amine bis(2-hydroxyarylmethyl) ligand precursor[CH$_3$—CH$_2$—CH$_2$—] 10

A mixture of 2,4-di-tert(butyl)phenol (5.0 g, 24.2 mmol), 1-aminopropane (1.0 mL, 12.1 mmol), and 36% aqueous formaldehyde (4.0 mL, 48.0 mmol) in methanol (10 mL), was stirred and refluxed for 24 hrs. The mixture was cooled in a freezer over night and the supernatant solution decanted. The residue was triturated using a triturating solvent such as ice cold methanol, filtered, and washed thoroughly with cold methanol, to give the bis-adduct 10 as a colorless powder (2.7 g, 45.4% yield), which could be further purified by re-crystallization from ethanol.

Melting point of 10 was 132° C.

HRMS (high resolution mass spectrometry) of 10: calculated, 495.407630, and observed, 495.406458.

Spectroscopic Data of 10. $^1$H NMR ($C_6D_6$, 200 MHz) δ8.21 (s, 2H, OH), 7.48 (d, J=2.3, 2H, Ar), 6.97 (d, J=2.3, 2H, Ar), 3.37 (s, 4H, $CH_2$), 2.19 (t, J=7.1, 2H, $CH_2$), 1.62 (s, 18H, $C(CH_3)_3$), 1.34 (s, 18H, $C(CH_3)_3$), 1.26 (m, 2H, $CH_2$), 0.57 (t, J=7.3, 3H, $CH_3$). $^{13}$C NMR ($CDCl_3$, 151.14 MHz), δ152.4, 141.5, 136.0, 125.0, 123, 121, 57.2 ($ArCH_2N$), 55.5 ($NCH_2$), 34.8 (C—C), 34 (C—C), 31.6 ($CH_3$), 29 ($CH_3$), 19.4 ($CH_2$), 11.7 ($CH_3$).

EXAMPLE 3

Synthesis of amine bis(2-hydroxyarylmethyl) ligand precursor [2-Pyridine-$CH_2$—] 12

A solution of 2,4-di-tert(butyl)phenol (5.0 g, 24.2 mmol), 2-(aminomethyl)pyridine (1.5 mL, 14.6 mmol) and 36% aqueous formaldehyde (2 mL, 24 mmol) in methanol (8 mL) was stirred and refluxed for 18 hrs. The mixture was cooled in a freezer over night and the supernatant solution decanted. The solid residue was triturated with ice cold methanol, filtered, and washed thoroughly with cold methanol, to give the bis-adduct 12 as a colorless powder (2.81 g, 42.6% yield), which could be further purified by recrystallization from methanol.

Melting point of 12 was 199° C.

HRMS of 12: Calculated, 545.410704, and observed, 545.410850.

Spectroscopic Data of 12. $^1$H NMR (acetone-$d_6$, 300 MHz) δ8.71 (d, 1H), 7.85 (t, 1H), 7.43 (t, 1H), 7.35 (d, 1H), 7.03 (d, J=1.2, 2H), 7.23 (d, J=1.2, 2H), 3.92 (s, 2H, $NCH_2Pr$), 3.83 (s, 4H, $ArCH_2N$), 1.39 (s, 18H, $C(CH_3)_3$), 1.27 (s, 18H, $C(CH_3)_3$). $^{13}$C NMR ($CDCl_3$, 90.68 MHz) δ156.2, 148.1, 137.3, 123.7, 122.4 (5C, pyridine ring), 153.8, 140.4, 136.3, 125.1, 123.4, 121.23 (12C, aromatic), 56.8 ($ArCH_2N$), 55.3 ($CH_2$), 35.06 (C—C), 34.1 (C—C), 31.7 ($CH_3$), 29.6 ($CH_3$).

EXAMPLE 4

Synthesis of amine bis(phenolate) ligand-metal chelate pre-catalyst [$(CH_3)_2$N—$CH_2$—$CH_2$—]—Zr$(CH_2Ph)_2$ 9

A solution of amine bis(2-hydroxyarylmethyl) ligand precursor [$(CH_3)_2$N—$CH_2$—$CH_2$—] 7, as synthesized according to Example 1, (200 mg, 0.38 mmol) in toluene (10 mL) was added drop-wise to a solution of zirconium tetra(benzyl) (0.38 mmol) in toluene (10 mL), at room temperature under nitrogen gas inert atmosphere. The reaction mixture was then heated to 65° C. and stirred for two hours. The toluene was removed from the reaction mixture under low pressure to yield pre-catalyst 9, 99% pure, as a yellow solid.

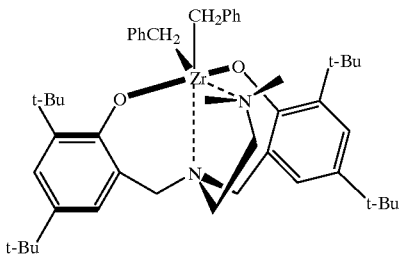

Spectroscopic Data of 9. $^1$H NMR ($C_6D_6$, 600 MHz) δ7.74 (d, J=7.1, 2H), 7.62 (d, J=2.4, 2H), 7.39 (t, J=8.1, 2H), 7.05 (t, J=7.3, 1H), 6.95 (d, J=2.4, 2H), 6.90 (d, J=7.1, 2H), 6.73 (t, J=8.0, 2H), 6.55 (t, J=7.3, 1H), 3.45 (br d, J=13.0, 2H, $CH_2$), 2.70 (s, 2H, $PhCH_2$), 2.60 (d, J=13.6, 2H, $CH_2$), 2.57 (s, 2H, $PhCH_2$), 1.88 (s, 18H, $CH_3$), 1.48 (s, 6H, $N(CH_3)_2$), 1.40 (br, 4H, $CH_2$), 1.36 (s, 18H, $CH_3$). $^{13}$C NMR ($C_6D_6$, 151.14 MHz) δ158.2, 149.3, 147.2, 141.3, 136.5, 129.1, 128.4, 128.3, 127.5, 125.2, 124.8, 122.5, 120.4, 68.1 ($PhCH_2$), 66.1 ($PhCH_2$), 65.2 ($ArCH_2N$), 60.2 ($NCH_2$), 51.9 ($NCH_2$), 47.5 ($N(CH_3)_2$), 35.7 (C—C), 34.4 (C—C), 32.0 ($CH_3$), 30.8 ($CH_3$).

Crystallographic (X-ray) Data for $C_{53}H_{80}N_2O_2Zr$ 9. M=868.41, monoclinic space group $P2_1/c$, a=18.4520(10), b=19.1310(19), c=28.2390(10) Å, β=90°, U=9968.5(8) Å$^3$, Z=8, $D_c$=1.157 g/cm$^3$, μ(Mo-Kα)=0.260 mm$^{-1}$, T=117 °K. Enraf-Nonius Kappa-CCD, 9375 reflections were measured ($R_{int}$=0.000). The structure was solved by direct methods and refined by full-matrix least-squares on F$^2$. In the crystal, the dimethylamino(ethyl) arm was found to be disordered. The unit cell contain one molecule of pentane. The final refinement converged at $R_1$=0.1028 and $wR_2$=0.2636 for observations with [I>2σ(1)] and $R_1$=0.1480 and $wR_2$=0.2853 for all data.

Spectroscopic data of 9 are consistent with a single stereoisomer featuring symmetrically related phenolate rings, two different benzyl groups, and an AX spin system for the two benzylic methylene groups. This points to a rigid chelate of $C_s$ symmetry on the NMR time scale, with the benzyl groups in a cis geometry, as required for alpha-olefin polymerization catalysts, and the phenolate groups in a trans geometry.

The crystallographic (X-ray) data support the spectroscopic data. The X-ray structure of pre-catalyst [$N(CH_3)_2$—$CH_2$—$CH_2$—]—Zr$(CH_2Ph)_2$ 9, shown in FIG. 1, indicates a structure featuring a mononuclear zirconium chelate having a slightly distorted octahedral geometry, including a coordinative bond between Zr and each of the two nitrogen atoms. The phenolate groups of the tetradentate ligand fold back toward the pendant (dimethylamino)ethyl arm to an extent the angle between the two planes of the phenolate rings is about 30 degrees, thus leaving a relatively open cleft for the equatorial benzyl group. The small difference between the two coordinative N—Zr bond lengths may indicate a weaker binding of the outer side arm nitrogen to the metal.

EXAMPLE 5

Synthesis of amine bis(phenolate) ligand-metal chelate pre-catalyst [$CH_3$—$CH_2$—$CH_2$—]—Zr$(CH_2Ph)_2$ 11

In addition to serving as another example of a specific form of general amine bis(phenolate) ligand-metal chelate catalyst 1, the five coordinate dialkyl amine bis(phenolate) ligand-metal chelate pre-catalyst, [CH$_3$—CH$_2$—CH$_2$—]—Zr(CH$_2$Ph)$_2$ 11, was synthesized in order to further understand and measure the influence of the 'extra' heteroatom, in (R$_n$Y—T) group, in the six coordinate dialkyl amine bis (phenolate) ligand-metal chelate pre-catalyst, [(CH$_3$)$_2$N—CH$_2$—CH$_2$—]—Zr(CH$_2$Ph)$_2$ 9, arising from inclusion of (CH$_3$)$_2$N—CH$_2$—CH$_2$— as (R$_n$Y—T) group in the amine bis(phenolate) ligand precursor bridging group, —CH$_2$—(R$_n$Y—T)N—CH$_2$—, for polymerization of alpha-olefin monomers.

A solution of amine bis(2-hydroxyarylmethyl) ligand precursor [CH$_3$—CH$_2$—CH$_2$—] 10, synthesized according to Example 2, (200 mg, 0.40 mmol) in toluene (10 mL) was added drop-wise to a solution of zirconium tetra(benzyl) (0.40 mmol) in toluene (10 mL), at room temperature under nitrogen gas inert atmosphere. The reaction mixture was then heated to 65° C. and stirred for two hours. The color of the reaction mixture changed from yellow to colorless. The toluene was removed from the reaction mixture under low pressure to yield pre-catalyst 11 , 99% pure, as a colorless solid.

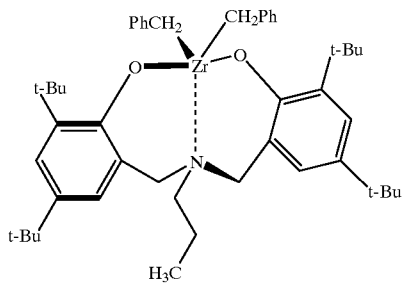

11

Spectroscopic Data of 11. $^1$H NMR (C$_6$D$_6$, 360 MHz) δ7.76 (d, J=7.5, 2H), 7.57 (d, J=2.3, 2H), 7.28 (t, J=7.6, 2H), 7.12 (t, J=7.3, 1H), 6.94 (d, J=2.3, 2H), 6.92 (d, J=7.4, 2H), 6.74 (t, J=7.4, 2H), 6.62 (t, J=7.3, 1H), 3.30 (d, J=13.8, 2H, CH$_2$), 2.99 (s, 2H, PhCH$_2$), 2.98 (d, J=13.6, 2H, CH$_2$), 2.03 (m, 2H, CH$_2$), 1.95 (s, 2H, PhCH$_2$), 1.79 (s, 18H, CH$_3$), 1.35 (s, 18H, CH$_3$), 1.05 (m, 2H, CH$_2$), −0.03 (t, J=7.3, CH$_3$). $^{13}$C NMR (C$_6$D$_6$, 90.68 MHz) δ158.3, 148.3, 142.1, 137.4, 136.8, 131.4, 129.5, 125.8, 125.4, 125.2, 125.1, 122.7, 60.9 (ArCH$_2$N, NCH$_2$), 58.9 (PhCH$_2$), 45.5 (PhCH$_2$), 36.1 (C—C), 35.0 (C—C), 32.6 (CH$_3$), 31.3 (CH$_3$), 14.0 (CH$_2$), 11.2 (CH$_3$).

Crystallographic (X-ray) Data for C$_{54}$H$_{81}$NO$_2$Zr 11. M=867.42, monoclinic space group P2$_1$/c, a=10.4840(1), b=19.2970(4), c=24.5940(5) Å, β=91.048(1)°, U=4974.77 (15) Å$^3$, Z=4 D$_c$=1.158 g/cm$^3$, μ(Mo-Kα)=0.259 mm$^{-1}$, T=116 °K. Enraf-Nonius Kappa-CCD, 12508 reflections were measured (R$_{int}$=0.000). The structure was solved by direct methods and refined by full-matrix least-squares on F$^2$. In the crystal, one of the tert-butyl groups was found to be disordered. The unit cell contains one molecule of heptane. The final refinement converged at R$_1$=0.0493 and wR$_2$=0.1295 for observations with [I>2σ(I)] and R$_1$=0.0624 and wR$_2$=0.1377 for all data.

Spectroscopic data of 11 are consistent with a single stereoisomer featuring symmetrically related phenolate rings, two different benzyl groups, and an AX spin system for the two benzylic methylene groups. This points to another rigid chelate of C$_s$ symmetry on the NMR time scale, with the benzyl groups in a non-trans geometry, as required for alpha-olefin polymerization catalysts, and the phenolate groups in a trans geometry.

The crystallographic (X-ray) data support the spectroscopic data. The X-ray structure of pre-catalyst [CH$_3$—CH$_2$—CH$_2$—]—Zr(CH$_2$Ph)$_2$ 11, shown in FIG. 2, indicates a structure featuring a mononuclear zirconium chelate having a pseudo trigonal bi-pyrimidal (TBP) geometry, with axial O atoms and equatorial N, C, C atoms. The two benzylic carbon atoms, the nitrogen atom and the metal atom, all lie in the same plane, as the sum of the (CH$_2$)$^1$—Zr—(CH$_2$)$^2$ angle (117.39°), the (CH$_2$)—Zr—N angle (114.45°) and the (CH$_2$)$^2$—Zr—N angle (128.15°) equals 360.0°. The acute Zr—(CH$_2$)—C(Ar) angle (89.4°), as well as the short Zr—C(Ar) distance (2.71 Å), for one of the benzyl groups, indicate that the pi-system of the benzyl ligand interacts with the metal center, namely, there is a non classical η$^2$ binding of this group to the Zr atom, as taught by Cloke, F. G. N. et al., in *J. Organomet. Chem.* 506, 343, 1996.

EXAMPLE 6

Synthesis of amine bis(phenolate) ligand-metal chelate pre-catalyst [2-Pyridine-CH$_2$—]—Zr(CH$_2$Ph)$_2$ 13

As another example of a specific form of general amine bis(phenolate) ligand-metal chelate catalyst 1, the six coordinate dialkyl amine bis(phenolate) ligand-metal chelate pre-catalyst, [2-Pyridine-CH$_2$—]—Zr(CH$_2$Ph)$_2$ 13, was synthesized.

A solution of amine bis(2-hydroxyarylmethyl) ligand precursor [2-Pyridine-CH$_2$—] 12, synthesized according to Example 3, (150 mg, 0.28 mmol) in toluene (5 mL), was added drop-wise to a solution of zirconium tetra(benzyl) (0.28 mmol) in toluene (5 mL), at room temperature under nitrogen gas inert atmosphere. The reaction mixture was then heated to 65° C. and stirred for two hours. The toluene was removed from the reaction mixture under low pressure to yield pre-catalyst 13 , 99% pure, as a yellow solid.

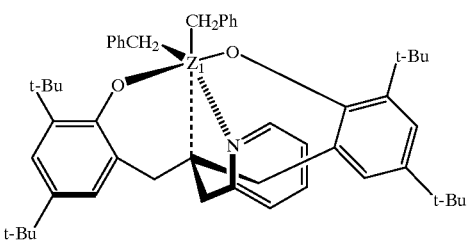

13

Spectroscopic Data of 13. $^1$H NMR (C$_6$D$_6$, 200 MHz) δ8.17 (d, J=5.2, 1H), 7.83 (d, J=7.6, 2H), 7.40 (t, J=7.6, 2H), 7.35 (d, J=2.3, 2H), 7.06 (m, 3H), 6.89 (t, J=7.3, 2H), 6.81 (d, J=2.3, 2H), 6.65 (t, J=7.2, 1H), 6.33 (t, J=7.5, 1H), 6.10 (t, J=6.1, 1H), 5.59 (d, J=7.7, 1H), 3.77 (d, J=13.1, 2H, CH$_2$), 3.23 (s, 2H, CH$_2$), 2.92 (s, 2H, CH$_2$), 2.63 (d, J=13.1, 2H, CH$_2$), 2.59 (s, 2H, CH$_2$), 2.06 (m, 2H, CH$_2$), 1.70 (s, 18H, CH$_3$), 1.34 (s, 18H, CH$_3$).

The spectroscopic data of 13 are consistent with a single stereoisomer featuring symmetrically related phenolate rings, two different benzyl groups, and an AX spin system for the two benzylic methylene groups. This points to another rigid chelate of C$_s$ symmetry on the NMR time scale, with the benzyl groups in a cis geometry, as required for alpha-olefin polymerization catalysts, and the phenolate groups in a trans geometry.

EXAMPLE 7

Polymerization of 1-hexene, in neat 1-hexene, using amine bis(phenolate) ligand-metal chelate pre-catalyst [(CH$_3$)$_2$N—CH$_2$—CH$_2$—]—Zr(CH$_2$Ph)$_2$ 9

A solution of co-catalyst B(C$_6$F$_5$)$_3$ (0.01 mmol) in 1-hexene (5 mL), was added drop-wise to a solution of pre-catalyst 9 (10 mg, 0.01 mmol) in 1-hexene (5 mL), at room temperature under nitrogen atmosphere. The reaction mixture was stirred for a couple of minutes, during which substantial heat was evolved, causing boiling of the 1-hexene, and reaction mixture color changed from yellow to colorless, and back to yellow. The small quantity of remaining 1-hexene monomer reactant/solvent was removed under low pressure to yield poly(1-hexene), 95%, as a colorless sticky oil.

Catalytic activity calculated from reaction data: 21,000 (grams poly(1-hexene) produced)/(mmole-pre-cat. hr).

Molecular weight obtained: M$_w$=12,700 grams/mole, with a PDI of 6.

Spectroscopic data of the poly(1-hexene) product. $^1$H NMR (CDCl$_3$, 200 MHz) δ1.23 (bs, 8H, CH$_2$), 1.06 (bs, 1H, CH), 0.89 (t, J=5.6, 3H, CH$_3$). $^{13}$C NMR (CDCl$_3$, 50.38 MHz) δ40.95 (br, CH$_2$), 35.04 (br, CH$_2$), 32.99 (CH), 29.39 (CH$_2$), 29.03 (CH$_2$), 24.01 (CH$_2$), 14.94 (CH$_3$).

EXAMPLE 8

Polymerization of 1-hexene, in dilute 1-hexene, using amine bis(phenolate) ligand-metal chelate pre-catalyst [(CH$_3$)$_2$N—CH$_2$—CH$_2$—]—Zr(CH$_2$Ph)$_2$ 9

A solution of co-catalyst B(C$_6$F$_5$)$_3$ (0.005 mmol) in 1-hexene (1 mL) and heptane (1 mL), was added drop-wise to a solution of pre-catalyst 9 (5 mg, 0.005 mmol) in 1-hexene (2 mL) and heptane (6 mL), at room temperature under nitrogen atmosphere. In each instance of dissolving pre-catalyst and co-catalyst, heptane was used as an inert diluent of 1-hexene reactant/solvent, leading to an initial reaction mixture heptane: 1-hexene volume ratio of 7:3. The reaction mixture was stirred for 8 minutes, during which evolution of heat was relatively mild compared to heat evolution during the polymerization reaction described in Example 7. Reaction mixture color changed from yellow to colorless. Remaining quantities of 1-hexene monomer reactant/solvent and of heptane diluent were removed under low pressure to yield poly(1-hexene), 85%, as a colorless sticky oil.

Catalytic activity calculated from reaction data: 2000 (grams poly(1-hexene) produced)/(mmole-pre-cat. hr). Time dependence of the consumption of 1-hexene monomer using pre-catalyst 9 activated in dilute 1-hexene solvent is shown in FIG. 3.

Molecular weight obtained: M$_w$=170,000 grams/mole, with a PDI of 2.2.

EXAMPLE 9

Polymerization of 1-hexene, in neat 1-hexene, using amine bis(phenolate) ligand-metal chelate pre-catalyst [CH$_3$—CH$_2$—CH$_2$—]—Zr(CH$_2$Ph)$_2$ 11

A solution of co-catalyst B(C$_6$F$_5$)$_3$ (0.01 mmol) in 1-hexene (1 mL), was added drop-wise to a solution of pre-catalyst 11 (10 mg, 0.01 mmol) in 1-hexene (1 mL), at room temperature under nitrogen atmosphere. The reaction mixture was stirred for a couple of minutes. The remaining 1-hexene monomer reactant/solvent was removed under low pressure to yield oligo(1-hexene) of about 20 monomers per chain, as a colorless sticky oil.

Catalytic activity calculated from reaction data: 23 (grams poly(1-hexene) produced)/(mmole-pre-cat. hr).

EXAMPLE 10

Polymerization of 1-hexene, in neat 1-hexene, using amine bis(phenolate) ligand-metal chelate pre-catalyst [2-Pyridine-CH$_2$—]—Zr(CH$_2$Ph)$_2$ 13

A solution of co-catalyst B(C$_6$F$_5$)$_3$ (0.01 mmol) in 1-hexene (1 mL), was added drop-wise to a solution of pre-catalyst 13 (10 mg, 0.01 mmol) in 1-hexene (1 mL), at room temperature under nitrogen atmosphere. The reaction mixture was stirred for a couple of minutes, during which substantial heat was evolved, causing boiling of the 1-hexene, and reaction mixture color changed from yellow to colorless, and back to yellow. The 1-hexene monomer was boiled and reaction mixture color changed from yellow to colorless, and back to yellow. The small quantity of remaining 1-hexene monomer reactant/solvent was removed under low pressure to yield poly(1-hexene), 95%, as a colorless sticky oil.

Catalytic activity calculated from reaction data: about 10,000 (grams poly(1-hexene) produced)/(mmole-pre-cat. hr).

While the invention has been described in conjunction with specific embodiments and examples thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method for catalytic polymerization of an alpha-olefin monomer comprising the steps of:

(a) providing a particular form of an amine bis(phenolate) pre-catalyst having a general structure selected from the group consisting of:

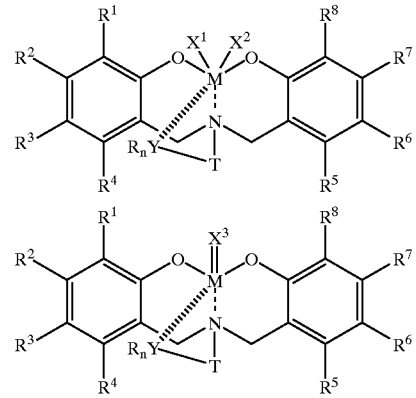

wherein:
a solid line represents a covalent bond;
a dashed line represents a bond having a varying degree of covalency and a varying degree of coordination;
M is a metal atom covalently bonded to each said O atom and bonded with varying degrees of covalency and coordination to said N atom;

$X^1$ and $X^2$ are each a univalent anionic ligand covalently bonded to said metal atom;

$X^3$ is a single divalent anionic ligand covalently bonded to said metal atom;

$R^1$ through $R^4$ are each a univalent radical covalently bonded to first said ($C_6$) aromatic group;

$R^5$ through $R^8$ are each a univalent radical covalently bonded to second said ($C_6$) aromatic group; and ($R_n$Y—T) is an optional group selected from the group consisting of a non-donor group covalently bonded to said N atom, wherein said non-donor group, said T is a covalent bridging group between said N atom and said Y, said Y is a group covalently bonded to said T, and, each of at least one said $R_n$ is selected from the group consisting of a saturated substituent covalently bonded to said Y, an unsaturated substituent covalently bonded to said Y, and a univalent radical covalently bonded to said Y, and a donor group covalently bonded to said N atom, wherein said donor group, said T is a covalent bridging group between said N atom and said Y, said Y is a heteroatom covalently bonded to said T and bonded with varying degrees of covalency and coordination to said metal atom, and, optional said $R_n$ substituents are selected from the group consisting of at least one saturated substituent covalently bonded to said Y, and at least one unsaturated substituent covalently bonded to said Y;

(b) preparing a first chemical entity featuring said particular form of said amine bis(phenolate) pre-catalyst of step (a);

(c) providing a co-catalyst suitable for activating said particular form of said amine bis(phenolate) pre-catalyst;

(d) preparing a second chemical entity featuring said provided co-catalyst of step (c);

(e) forming a catalytic polymerization reaction by mixing (i) said first chemical entity featuring said particular form of said amine bis(phenolate) pre-catalyst, with (ii) said second chemical entity of said provided co-catalyst, with (iii) the alpha-olefin monomer to be catalytically polymerized, whereby said co-catalyst activates said pre-catalyst, whereby combination of said pre-catalyst and said co-catalyst becomes a catalyst for effecting the catalytic polymerization of the alpha-olefin monomer and for producing at least one poly(alpha-olefin) product;

(f) allowing said catalytic polymerization reaction to progress;

(g) terminating said catalytic polymerization reaction; and (h) isolating said at least one poly(alpha-olefin) product formed by said catalytic polymerization reaction.

2. The method of claim 1, wherein said pre-catalyst, said metal atom is a transition metal atom.

3. The method of claim 1, wherein said pre-catalyst, said metal atom is a transition metal atom selected from the group consisting of zirconium, hafnium, and titanium.

4. The method of claim 1, wherein said pre-catalyst, $X^1$ and said $X^2$ are each selected from the group consisting of a halide, a hydride, a saturated hydrocarbyl, an unsaturated hydrocarbyl, an alkoxide, an aryloxide, a dialkylamide, and an arylamide.

5. The method of claim 1, wherein said pre-catalyst, $X^3$ is selected from the group consisting of a cyclometallated hydrocarbyl, and a radical, said radical including an alkylidene.

6. The method of claim 1, wherein said pre-catalyst, each of said $R^1$ through $R^4$ is selected from the group consisting of a hydrogen radical, a hydrocarbyl radical, and an alkoxide radical.

7. The method of claim 1, wherein said pre-catalyst, each of said $R^5$ through $R^8$ is selected from the group consisting of a hydrogen radical, a hydrocarbyl radical, and an alkoxide radical.

8. The method of claim 1, wherein said pre-catalyst includes said ($R_n$Y—T) group as a said non-donor group, wherein said T is a said covalent bridging group selected from the group consisting of a saturated hydrocarbyl and an unsaturated hydrocarbyl.

9. The method of claim 1, wherein said pre-catalyst includes said ($R_n$Y—T) group as a said non-donor group, wherein said Y is selected from the group consisting of a saturated hydrocarbyl and an unsaturated hydrocarbyl.

10. The method of claim 1, wherein said pre-catalyst includes said ($R_n$Y—T) group as a said non-donor group, wherein said each of at least one $R_n$ is a said saturated substituent selected from the group consisting of a methyl substituent and an ethyl substituent.

11. The method of claim 1, wherein said pre-catalyst includes said ($R_n$Y—T) group as a said non-donor group, wherein said each of at least one $R_n$ is a said univalent radical selected from the group consisting of a hydrogen radical and a methyl radical.

12. The method of claim 1, wherein said pre-catalyst includes said ($R_n$Y—T) group as a said donor group, wherein said T is a said covalent bridging group selected from the group consisting of a saturated hydrocarbyl, an unsaturated hydrocarbyl, and a part of an aromatic system.

13. The method of claim 12, wherein said saturated hydrocarbyl is selected from the group consisting of a methyl group and an ethyl group.

14. The method of claim 12, wherein said unsaturated hydrocarbyl is an ethylene group.

15. The method of claim 12, wherein said aromatic system is a pyridine ring.

16. The method of claim 1, wherein said pre-catalyst includes said ($R_n$Y—T) group as a said donor group, wherein said Y is a said heteroatom selected from the group consisting of nitrogen, oxygen, sulfur, and phosphorous.

17. The method of claim 1, wherein said pre-catalyst includes said ($R_n$Y—T) group as a said donor group, wherein said optional $R_n$ substituents are said at least one said saturated substituent selected from the group consisting of a methyl substituent and an ethyl substituent.

18. The method of claim 1, wherein said pre-catalyst includes said ($R_n$Y—T) group as a said donor group, wherein said optional $R_n$ substituents are said at least one said unsaturated substituent, said unsaturated substituent includes a part of an aromatic system.

19. The method of claim 1, wherein a particular form of said general structure of said amine bis(phenolate) pre-catalyst is selected from the group consisting of [($CH_3$)$_2$N—$CH_2$—$CH_2$—]—Zr($CH_2$Ph)$_2$, [$CH_3$—$CH_2$—$CH_2$—]—Zr($CH_2$Ph)$_2$, [2-Pyridine-$CH_2$—]—Zr($CH_2$Ph)$_2$, [($CH_3$)$_2$N—$CH_2$—$CH_2$—]—Ti($CH_2$Ph)$_2$, [($CH_3$)O—$CH_2$—$CH_2$—]—Ti($CH_2$Ph)$_2$, [($CH_3CH_2$)$_2$N—$CH_2$—$CH_2$—]—Zr($CH_2$Ph)$_2$, and, [2-Pyridine-$CH_2$—$CH_2$—]—Zr($CH_2$Ph)$_2$.

20. The method of claim 1, wherein step (b) includes mixing said particular form of said pre-catalyst with an organic solvent for said preparing said first chemical entity in a form selected from the group consisting of a suspension and a solution.

21. The method of claim 20, wherein said organic solvent is liquid form of the alpha-olefin monomer to be polymerized, said organic solvent is selected from the group consisting of ethylene (liquid phase), propylene (liquid phase), 1-pentene, 1-hexene, 1-octene, 1,5-hexadiene, and, a higher alpha-olefin monomer.

22. The method of claim 20, wherein said organic solvent is liquid form of the alpha-olefin monomer to be polymerized, said organic solvent is selected from the group consisting of ethylene (liquid phase), propylene (liquid phase), 1-pentene, 1-hexene, 1-octene, 1,5-hexadiene, and, a higher alpha-olefin monomer, mixed with at least one additional organic solvent not including the alpha-olefin monomer to be polymerized, said at least one additional organic solvent is selected from the group consisting of pentane, heptane, toluene, methylene chloride, and, chlorobenzene, whereby said at least one additional organic solvent not including the alpha-olefin monomer functions as an inert diluent in said catalytic polymerization reaction.

23. The method of claim 1, wherein step (b) includes exposing said first chemical entity to a surface of at least one solid substrate for preparing an adsorbed state of said first chemical entity.

24. The method of claim 23, wherein said at least one solid substrate is selected from the group consisting of a silica solid substrate, an alumina solid substrate, a magnesia solid substrate, and, a combination solid substrate.

25. The method of claim 1, wherein step (c), said co-catalyst is selected from the group consisting of a boron Lewis acid co-catalyst, a boron salt co-catalyst, and, an aluminum compound co-catalyst.

26. The method of claim 1, wherein step (c), said co-catalyst is selected from the group consisting of boron Lewis acid tris(pentafluorophenyl)boron $B(C_6F_5)_3$ co-catalyst, boron salt N,N'-dimethyl anilinium tetrakis (penta-fluoro-phenyl)borate co-catalyst, $[Ph(CH_3)_2NH][B(C_6F_5)_4]$ co-catalyst, and, aluminum compound methylaluminoxane (MAO) co-catalyst.

27. The method of claim 1, wherein step (d) includes mixing said provided co-catalyst with an organic solvent for said preparing said second chemical entity in a form selected from the group consisting of a suspension and a solution.

28. The method of claim 27, wherein said organic solvent is liquid form of the alpha-olefin monomer to be polymerized, said organic solvent is selected from the group consisting of ethylene (liquid phase), propylene (liquid phase), 1-pentene, 1-hexene, 1-octene, 1,5-hexadiene, and, a higher alpha-olefin monomer.

29. The method of claim 27, wherein said organic solvent is liquid form of the alpha-olefin monomer to be polymerized, said organic solvent is selected from the group consisting of ethylene (liquid phase), propylene (liquid phase), 1-pentene, 1-hexene, 1-octene, 1,5-hexadiene, and, a higher alpha-olefin monomer, mixed with at least one additional organic solvent not including the alpha-olefin monomer to be polymerized, said at least one additional organic solvent is selected from the group consisting of pentane, heptane, toluene, methylene chloride, and, chlorobenzene, whereby said at least one additional organic solvent not including the alpha-olefin monomer functions as an inert diluent in said catalytic polymerization reaction.

30. The method of claim 1, wherein step (d) includes exposing said second chemical entity to a surface of at least one solid substrate for preparing an adsorbed state of said second chemical entity.

31. The method of claim 30, wherein said at least one solid substrate is selected from the group consisting of a silica solid substrate, an alumina solid substrate, a magnesia solid substrate, and, a combination thereof.

32. The method of claim 1, whereby step (e) is independent of order of said mixing said first chemical entity of said pre-catalyst, with said second chemical entity of said co-catalyst, with the alpha-olefin monomer to be catalytically polymerized.

33. The method of claim 1, wherein conditions for performing step (a) through step (e) include a pressure range of from about 1 bar to about 30 bar and a temperature range of from about −78° C. to about 150° C., with exclusion of moisture and oxygen.

34. The method of claim 1, wherein conditions for performing step (a) through step (e) include a pressure range of from about 1 bar to about 5.5 bar and a temperature range of from about 20° C. to about 30° C., with exclusion of moisture and oxygen.

35. The method of claim 1, wherein step (f) includes adding to said catalytic polymerization reaction at least one other type and quantity of a chemical reagent for improving the catalytic polymerization of the alpha-olefin monomer.

36. The method of claim 1, wherein step (f) further includes adding hydrogen gas to said catalytic polymerization reaction for improving control of molecular weight of said at least one poly(alpha-olefin) product.

37. The method of claim 1, wherein step (g), said terminating said catalytic polymerization reaction is performed by involving means selected from the group consisting of means initially external to said catalytic polymerization reaction, means internal to said catalytic polymerization reaction, and, a combination thereof, said external means is selected from the group consisting of adding an external quencher to said catalytic polymerization reaction, removing remaining alpha-olefin monomer from said catalytic polymerization reaction, and, a combination thereof, said internal means is selected from the group consisting of complete consumption of the alpha-olefin monomer, deactivation of said catalyst formed during said progression of said catalytic polymerization reaction, and, a combination thereof.

38. The method of claim 1, whereby said catalytic polymerization reaction is formed and progresses in a type of chemical reactor selected from the group consisting of a continuous flow chemical reactor, a batch chemical reactor, and, a plug-flow chemical reactor, where size of said chemical reactor is selected from the group consisting of a micro-scale laboratory chemical reactor, a product/process development scale chemical reactor, and a large scale commercial chemical reactor.

39. The method of claim 1, whereby said catalytic polymerization reaction is a type of chemical process selected from the group consisting of a continuous flow chemical process, a batch chemical process, and, a plug-flow chemical process, said chemical process is of a size selected from the group consisting of a micro-scale laboratory chemical process, a product/process development scale chemical process, and, a large scale commercial chemical process.

40. The method of claim 1, whereby said catalytic polymerization reaction features living polymerization of the alpha-olefin monomer.

41. The method of claim 40, whereby said at least one poly(alpha-olefin) product is produced having a molecular weight of about 450,000 grams/mole in a living fashion.

42. The method of claim 40, whereby said at least one poly(alpha-olefin) product is produced having a molecular weight of about 450,000 grams/mole in a living fashion with a polydispersity index (PDI) of about 1.1.

43. The method of claim 1, whereby said catalytic polymerization reaction is formed and progresses in a temperature range of from about 20° C. to about 50° C. and features living polymerization of the alpha-olefin monomer.

44. The method of claim 1, whereby said catalytic polymerization reaction is formed and progresses in a temperature range of from about 20° C. to about 50° C., features living polymerization of the alpha-olefin monomer, whereby said catalyst formed during said catalytic polymerization reaction remains living for a period of time of about 30 hours.

45. The method of claim 1, whereby said catalytic polymerization reaction features living polymerization while achieving block co-polymerization of the alpha-olefin monomer.

46. The method of claim 1, whereby said catalytic polymerization reaction is formed and progresses in a temperature range of from about 20° C. to about 50° C. and features living polymerization while achieving block co-polymerization of the alpha-olefin monomer.

47. The method of claim 1, wherein the alpha-olefin monomer is selected from the group consisting of ethylene, propylene, 1-pentene, 1-hexene, 1-octene, 1,5-hexadiene, and, a higher alpha-olefin monomer.

48. A method for catalytic polymerization of an alpha-olefin monomer comprising the steps of:

(a) providing a particular form of an amine bis(phenolate) catalyst having a general structure selected from the group consisting of:

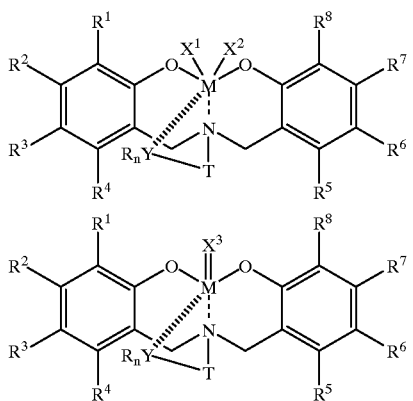

wherein:
a solid line represents a covalent bond;
a dashed line represents a bond having a varying degree of covalency and a varying degree of coordination;
M is a metal atom covalently bonded to each said O atom and bonded with varying degrees of covalency and coordination to said N atom;
$X^1$ and $X^2$ are each a univalent anionic ligand covalently bonded to said metal atom;
$X^3$ is a single divalent anionic ligand covalently bonded to said metal atom;
$R^1$ through $R^4$ are each a univalent radical covalently bonded to first said ($C_6$) aromatic group;
$R^5$ through $R^8$ are each a univalent radical covalently bonded to second said ($C_6$) aromatic group; and
($R_n$Y—T) is an optional group selected from the group consisting of a non-donor group covalently bonded to said N atom, wherein said non-donor group, said T is a covalent bridging group between said N atom and said Y, said Y is a group covalently bonded to said T, and, each of at least one said $R_n$ is selected from the group consisting of a saturated substituent covalently bonded to said Y, an unsaturated substituent covalently bonded to said Y, and a univalent radical covalently bonded to said Y, and a donor group covalently bonded to said N atom, wherein said donor group, said T is a covalent bridging group between said N atom and said Y, said Y is a heteroatom covalently bonded to said T and bonded with varying degrees of covalency and coordination to said metal atom, and, optional said Rn substituents are selected from the group consisting of at least one saturated substituent covalently bonded to said Y, and at least one unsaturated substituent covalently bonded to said Y;

(b) preparing a first chemical entity featuring said particular form of said amine bis(phenolate) catalyst of step (a);

(c) forming a catalytic polymerization reaction by mixing (i) said first chemical entity featuring said particular form of said amine bis(phenolate) catalyst, with (ii) the alpha-olefin monomer to be catalytically polymerized, whereby said amine bis(phenolate) catalyst effects the catalytic polymerization of the alpha-olefin monomer for producing at least one poly(alpha-olefin) product;

(d) allowing said catalytic polymerization reaction to progress;

(e) terminating said catalytic polymerization reaction; and (f) isolating said at least one poly(alpha-olefin) product formed by said catalytic polymerization reaction.

49. The method of claim 48, wherein said catalyst, said metal atom is a transition metal atom.

50. The method of claim 48, wherein said catalyst, said metal atom is a transition metal atom selected from the group consisting of zirconium, hafnium, and titanium.

51. The method of claim 48, wherein said catalyst, said $X^1$ and said $X^2$ are each selected from the group consisting of a halide, a hydride, a saturated hydrocarbyl, an unsaturated hydrocarbyl, an alkoxide, an aryloxide, a dialkylamide, and an arylamide.

52. The method of claim 48, wherein said catalyst, said $X^3$ is selected from the group consisting of a cyclometallated hydrocarbyl, and a radical, said radical including an alkylidene.

53. The method of claim 48, wherein said catalyst, each of said $R^1$ through $R^4$ is selected from the group consisting of a hydrogen radical, a hydrocarbyl radical, and an alkoxide radical.

54. The method of claim 48, wherein said catalyst, each of said $R^5$ through $R^8$ is selected from the group consisting of a hydrogen radical, a hydrocarbyl radical, and an alkoxide radical.

55. The method of claim 48, wherein said catalyst includes said ($R_n$Y—T) group as a said non-donor group, wherein said T is a said covalent bridging group selected from the group consisting of a saturated hydrocarbyl and an unsaturated hydrocarbyl.

56. The method of claim 48, wherein said catalyst includes said ($R_n$Y—T) group as a said non-donor group, wherein said Y is selected from the group consisting of a saturated hydrocarbyl and an unsaturated hydrocarbyl.

57. The method of claim 48, wherein said catalyst includes said ($R_n$Y—T) group as a said non-donor group, wherein said each of at least one $R_n$ is a said saturated substituent selected from the group consisting of a methyl substituent and an ethyl substituent.

58. The method of claim 48, wherein said catalyst includes said ($R_n$Y—T) group as a said non-donor group, wherein said each of at least one $R_n$ is a said univalent radical selected from the group consisting of a hydrogen radical and a methyl radical.

59. The method of claim 48, wherein said catalyst includes said ($R_n$Y—T) group as a said donor group, wherein said T is a said covalent bridging group selected from the group consisting of a saturated hydrocarbyl, an unsaturated hydrocarbyl, and a part of an aromatic system.

60. The method of claim 59, wherein said saturated hydrocarbyl is selected from the group consisting of a methyl group and an ethyl group.

61. The method of claim 59, wherein said unsaturated hydrocarbyl is an ethylene group.

62. The method of claim 59, wherein said aromatic system is a pyridine ring.

63. The method of claim 48, wherein said catalyst includes said ($R_n$Y—T) group as a said donor group, wherein said Y is a said heteroatom selected from the group consisting of nitrogen, oxygen, sulfur, and phosphorous.

64. The method of claim 48, wherein said catalyst includes said ($R_n$Y—T) group as a said donor group, wherein said optional $R_n$ substituents are said at least one said saturated substituent selected from the group consisting of a methyl substituent and an ethyl substituent.

65. The method of claim 48, wherein said catalyst includes said ($R_n$Y—T) group as a said donor group, wherein said optional $R_n$ substituents are said at least one said unsaturated substituent, said unsaturated substituent includes a part of an aromatic system.

66. The method of claim 48, wherein a particular form of said general structure of said amine bis(phenolate) catalyst is selected from the group consisting of [($CH_3$)$_2$N—$CH_2$—$CH_2$—]—Zr($CH_2$Ph)$_2$, [$CH_3$—$CH_2$—$CH_2$—]—Zr($CH_2$Ph)$_2$, [2-Pyridine-$CH_2$—]—Zr($CH_2$Ph)$_2$, [($CH_3$)$_2$N—$CH_2$—$CH_2$—]—Ti($CH_2$Ph)$_2$, [($CH_3$)O—$CH_2$—$CH_2$—]—Ti($CH_2$Ph)$_2$, [($CH_3CH_2$)$_2$N—$CH_2$—$CH_2$—]—Zr($CH_2$Ph)$_2$, and, [2-Pyridine-$CH_2$—$CH_2$—]—Zr($CH_2$Ph)$_2$.

67. The method of claim 48, wherein step (b) includes mixing said particular form of said catalyst with an organic solvent for said preparing said first chemical entity in a form selected from the group consisting of a suspension and a solution.

68. The method of claim 67, wherein said organic solvent is liquid form of the alpha-olefin monomer to be polymerized, said organic solvent is selected from the group consisting of ethylene (liquid phase), propylene (liquid phase), 1-pentene, 1-hexene, 1-octene, 1,5-hexadiene, and, a higher alpha-olefin monomer.

69. The method of claim 67, wherein said organic solvent is liquid form of the alpha-olefin monomer to be polymerized, said organic solvent is selected from the group consisting of ethylene (liquid phase), propylene (liquid phase), 1-pentene, 1-hexene, 1-octene, 1,5-hexadiene, and, a higher alpha-olefin monomer, mixed with at least one additional organic solvent not including the alpha-olefin monomer to be polymerized, said at least one additional organic solvent is selected from the group consisting of pentane, heptane, toluene, methylene chloride, and, chlorobenzene, whereby said at least one additional organic solvent not including the alpha-olefin monomer functions as an inert diluent in said catalytic polymerization reaction.

70. The method of claim 48, wherein step (b) includes exposing said first chemical entity to a surface of at least one solid substrate for preparing an adsorbed state of said first chemical entity.

71. The method of claim 70, wherein said at least one solid substrate is selected from the group consisting of a silica solid substrate, an alumina solid substrate, a magnesia solid substrate, and, a combination solid substrate.

72. The method of claim 48, whereby step (c) is independent of order of said mixing said first chemical entity of said catalyst with the alpha-olefin monomer to be catalytically polymerized.

73. The method of claim 48, wherein conditions for performing step (a) through step (c) include a pressure range of from about 1 bar to about 30 bar and a temperature range of from about −78° C. to about 150° C., with exclusion of moisture and oxygen.

74. The method of claim 48, wherein conditions for performing step (a) through step (c) include a pressure range of from about 1 bar to about 5.5 bar and a temperature range of from about 20° C. to about 30° C., with exclusion of moisture and oxygen.

75. The method of claim 48, wherein step (d) includes adding to said catalytic polymerization reaction at least one other type and quantity of a chemical reagent for improving the catalytic polymerization of the alpha-olefin monomer.

76. The method of claim 48, wherein step (d) further includes adding hydrogen gas to said catalytic polymerization reaction for improving control of molecular weight of said at least one poly(alpha-olefin) product.

77. The method of claim 48, wherein step (e), said terminating said catalytic polymerization reaction is performed by involving means selected from the group consisting of means initially external to said catalytic polymerization reaction, means internal to said catalytic polymerization reaction, and, a combination thereof, said external means is selected from the group consisting of adding an external quencher to said catalytic polymerization reaction, removing remaining alpha-olefin monomer from said catalytic polymerization reaction, and, a combination thereof, said internal means is selected from the group consisting of complete consumption of the alpha-olefin monomer, deactivation of said catalyst formed during said progression of said catalytic polymerization reaction, and, a combination thereof.

78. The method of claim 48, whereby said catalytic polymerization reaction is formed and progresses in a type of chemical reactor selected from the group consisting of a continuous flow chemical reactor, a batch chemical reactor, and, a plug-flow chemical reactor, where size of said chemical reactor is selected from the group consisting of a micro-scale laboratory chemical reactor, a product/process development scale chemical reactor, and a large scale commercial chemical reactor.

79. The method of claim 48, whereby said catalytic polymerization reaction is a type of chemical process selected from the group consisting of a continuous flow chemical process, a batch chemical process, and, a plug-flow chemical process, said chemical process is of a size selected from the group consisting of a micro-scale laboratory chemical process, a product/process development scale chemical process, and, a large scale commercial chemical process.

80. The method of claim 48, whereby said catalytic polymerization reaction features living polymerization of the alpha-olefin monomer.

81. The method of claim 48, whereby said catalytic polymerization reaction is formed and progresses in a temperature range of from about 20° C. to about 50° C. and features living polymerization of the alpha-olefin monomer.

82. The method of claim 48, whereby said catalytic polymerization reaction is formed and progresses in a temperature range of from about 20° C. to about 50° C., features living polymerization of the alpha-olefin monomer, whereby said catalyst remains living for a period of time of about 30 hours.

83. The method of claim 48, whereby said catalytic polymerization reaction features living polymerization while achieving block co-polymerization of the alpha-olefin monomer.

84. The method of claim 48, whereby said catalytic polymerization reaction is formed and progresses in a temperature range of from about 20° C. to about 50° C. and features living polymerization while achieving block co-polymerization of the alpha-olefin monomer.

85. The method of claim 48, wherein the alpha-olefin monomer is selected from the group consisting of ethylene, propylene, 1-pentene, 1-hexene, 1-octene, 1,5-hexadiene, and, a higher alpha-olefin monomer.

86. A method for living catalytic polymerization of an alpha-olefin monomer comprising the steps of:

(a) providing a particular form of an amine bis(phenolate) pre-catalyst having a general structure selected from the group consisting of:

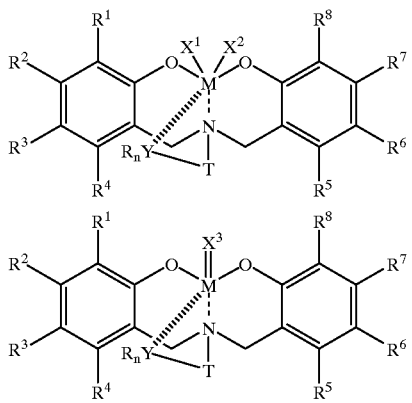

wherein:
a solid line represents a covalent bond;
a dashed line represents a bond having a varying degree of covalency and a varying degree of coordination;
M is a metal atom covalently bonded to each said O atom and bonded with varying degrees of covalency and coordination to said N atom;
$X^1$ and $X^2$ are each a univalent anionic ligand covalently bonded to said metal atom;
$X^3$ is a single divalent anionic ligand covalently bonded to said metal atom;
$R^1$ through $R^4$ are each a univalent radical covalently bonded to first said ($C_6$) aromatic group;
$R^5$ through $R^8$ are each a univalent radical covalently bonded to second said ($C_6$) aromatic group; and
($R_n$Y—T) is an optional group selected from the group consisting of a non-donor group covalently bonded to said N atom, wherein said non-donor group, said T is a covalent bridging group between said N atom and said Y, said Y is a group covalently bonded to said T, and, each of at least one said $R_n$ is selected from the group consisting of a saturated substituent covalently bonded to said Y, an unsaturated substituent covalently bonded to said Y, and a univalent radical covalently bonded to said Y, and a donor group covalently bonded to said N atom, wherein said donor group, said T is a covalent bridging group between said N atom and said Y, said Y is a heteroatom covalently bonded to said T and bonded with varying degrees of covalency and coordination to said metal atom, and, optional said Rn substituents are selected from the group consisting of at least one saturated substituent covalently bonded to said Y, and at least one unsaturated substituent covalently bonded to said Y;

(b) preparing a first chemical entity featuring said particular form of said amine bis(phenolate) pre-catalyst of step (a);

(c) providing a co-catalyst suitable for activating said particular form of said amine bis(phenolate) pre-catalyst;

(d) preparing a second chemical entity featuring said provided co-catalyst of step (c);

(e) forming a living catalytic polymerization reaction by mixing (i) said first chemical entity featuring said particular form of said amine bis(phenolate) pre-catalyst, with (ii) said second chemical entity of said provided co-catalyst, with (iii) the alpha-olefin monomer to be catalytically polymerized, whereby said co-catalyst activates said pre-catalyst, whereby combination of said pre-catalyst and said co-catalyst becomes a catalyst for effecting the living catalytic polymerization of the alpha-olefin monomer and for producing at least one poly(alpha-olefin) product;

(f) allowing said living catalytic polymerization reaction to progress;

(g) terminating said living catalytic polymerization reaction; and (h) isolating said at least one poly(alpha-olefin) product formed by said living catalytic polymerization reaction.

87. The method of claim 86, wherein said pre-catalyst, said metal atom is a transition metal atom.

88. The method of claim 86, wherein said pre-catalyst, said metal atom is a transition metal atom selected from the group consisting of zirconium, hafnium, and titanium.

89. The method of claim 86, wherein said pre-catalyst, said $X^1$ and said $X^2$ are each selected from the group consisting of a halide, a hydride, a saturated hydrocarbyl, an unsaturated hydrocarbyl, an alkoxide, an aryloxide, a dialkylamide, and an arylamide.

90. The method of claim 86, wherein said pre-catalyst, said $X^3$ is selected from the group consisting of a cyclometallated hydrocarbyl, and a radical, said radical including an alkylidene.

91. The method of claim 86, wherein said pre-catalyst, each of said $R^1$ through $R^4$ is selected from the group consisting of a hydrogen radical, a hydrocarbyl radical, and an alkoxide radical.

92. The method of claim 86, wherein said pre-catalyst, each of said $R^5$ through $R^8$ is selected from the group consisting of a hydrogen radical, a hydrocarbyl radical, and an alkoxide radical.

93. The method of claim 86, wherein said pre-catalyst includes said ($R_n$Y—T) group as a said non-donor group, wherein said T is a said covalent bridging group selected from the group consisting of a saturated hydrocarbyl and an unsaturated hydrocarbyl.

94. The method of claim 86, wherein said pre-catalyst includes said ($R_n$Y—T) group as a said non-donor group, wherein said Y is selected from the group consisting of a saturated hydrocarbyl and an unsaturated hydrocarbyl.

95. The method of claim 86, wherein said pre-catalyst includes said ($R_n$Y—T) group as a said non-donor group, wherein said each of at least one $R_n$ is a said saturated substituent selected from the group consisting of a methyl substituent and an ethyl substituent.

96. The method of claim 86, wherein said pre-catalyst includes said ($R_n$Y—T) group as a said non-donor group, wherein said each of at least one $R_n$ is a said univalent radical selected from the group consisting of a hydrogen radical and a methyl radical.

97. The method of claim 86, wherein said pre-catalyst includes said ($R_n$Y—T) group as a said donor group, wherein said T is a said covalent bridging group selected from the group consisting of a saturated hydrocarbyl, an unsaturated hydrocarbyl, and a part of an aromatic system.

98. The method of claim 86, wherein said saturated hydrocarbyl is selected from the group consisting of a methyl group and an ethyl group.

99. The method of claim 86, wherein said unsaturated hydrocarbyl is an ethylene group.

100. The method of claim 86, wherein said aromatic system is a pyridine ring.

101. The method of claim 86, wherein said pre-catalyst includes said ($R_n Y$—T) group as a said donor group, wherein said Y is a said heteroatom selected from the group consisting of nitrogen, oxygen, sulfur, and phosphorous.

102. The method of claim 86, wherein said pre-catalyst includes said ($R_n Y$—T) group as a said donor group, wherein said optional $R_n$ substituents are said at least one said saturated substituent selected from the group consisting of a methyl substituent and an ethyl substituent.

103. The method of claim 86, wherein said pre-catalyst includes said ($R_n Y$—T) group as a said donor group, wherein said optional $R_n$ substituents are said at least one said unsaturated substituent, said unsaturated substituent includes a part of an aromatic system.

104. The method of claim 86, wherein a particular form of said general structure of said amine bis(phenolate) pre-catalyst is selected from the group consisting of [($CH_3)_2N$—$CH_2$—$CH_2$—]—$Zr(CH_2Ph)_2$, [$CH_3$—$CH_2$—$CH_2$—]—$Zr(CH_2Ph)_2$, [2-Pyridine-$CH_2$—]—$Zr(CH_2Ph)_2$, [($CH_3)_2N$—$CH_2$—$CH_2$—]—$Ti(CH_2Ph)_2$, [($CH_3)O$—$CH_2$—$CH_2$—]—$Ti(CH_2Ph)_2$, [($CH_3CH_2)_2N$—$CH_2$—$CH_2$—]—$Zr(CH_2Ph)_2$, and, [2-Pyridine-$CH_2$—$CH_2$—]—$Zr(CH_2Ph)_2$.

105. The method of claim 86, wherein step (b) includes mixing said particular form of said pre-catalyst with an organic solvent for said preparing said first chemical entity in a form selected from the group consisting of a suspension and a solution.

106. The method of claim 105, wherein said organic solvent is liquid form of the alpha-olefin monomer to be polymerized, said organic solvent is selected from the group consisting of ethylene (liquid phase), propylene (liquid phase), 1-pentene, 1-hexene, 1-octene, 1,5-hexadiene, and, a higher alpha-olefin monomer.

107. The method of claim 105, wherein said organic solvent is liquid form of the alpha-olefin monomer to be polymerized, said organic solvent is selected from the group consisting of ethylene (liquid phase), propylene (liquid phase), 1-pentene, 1-hexene, 1-octene, 1,5-hexadiene, and, a higher alpha-olefin monomer, mixed with at least one additional organic solvent not including the alpha-olefin monomer to be polymerized, said at least one additional organic solvent is selected from the group consisting of pentane, heptane, toluene, methylene chloride, and, chlorobenzene, whereby said at least one additional organic solvent not including the alpha-olefin monomer functions as an inert diluent in said catalytic polymerization reaction.

108. The method of claim 86, wherein step (b) includes exposing said first chemical entity to a surface of at least one solid substrate for preparing an adsorbed state of said first chemical entity.

109. The method of claim 108, wherein said at least one solid substrate is selected from the group consisting of a silica solid substrate, an alumina solid substrate, a magnesia solid substrate, and, a combination solid substrate.

110. The method of claim 86, wherein step (c), said co-catalyst is selected from the group consisting of a boron Lewis acid co-catalyst, a boron salt co-catalyst, and, an aluminum compound co-catalyst.

111. The method of claim 86, wherein step (c), said co-catalyst is selected from the group consisting of boron Lewis acid tris(pentafluorophenyl)boron $B(C_6F_5)_3$ co-catalyst, boron salt N,N'-dimethyl anilinium tetrakis (penta-fluoro-phenyl)borate co-catalyst, [$Ph(CH_3)_2NH$][$B(C_6F_5)_4$] co-catalyst, and, aluminum compound methylaluminoxane (MAO) co-catalyst.

112. The method of claim 86, wherein step (d) includes mixing said provided co-catalyst with an organic solvent for said preparing said second chemical entity in a form selected from the group consisting of a suspension and a solution.

113. The method of claim 112, wherein said organic solvent is liquid form of the alpha-olefin monomer to be polymerized, said organic solvent is selected from the group consisting of ethylene (liquid phase), propylene (liquid phase), 1-pentene, 1-hexene, 1-octene, 1,5-hexadiene, and, a higher alpha-olefin monomer.

114. The method of claim 112, wherein said organic solvent is liquid form of the alpha-olefin monomer to be polymerized, said organic solvent is selected from the group consisting of ethylene (liquid phase), propylene (liquid phase), 1-pentene, 1-hexene, 1-octene, 1,5-hexadiene, and, a higher alpha-olefin monomer, mixed with at least one additional organic solvent not including the alpha-olefin monomer to be polymerized, said at least one additional organic solvent is selected from the group consisting of pentane, heptane, toluene, methylene chloride, and, chlorobenzene, whereby said at least one additional organic solvent not including the alpha-olefin monomer functions as an inert diluent in said catalytic polymerization reaction.

115. The method of claim 86, wherein step (d) includes exposing said second chemical entity to a surface of at least one solid substrate for preparing an adsorbed state of said second chemical entity.

116. The method of claim 115, wherein said at least one solid substrate is selected from the group consisting of a silica solid substrate, an alumina solid substrate, a magnesia solid substrate, and, a combination thereof.

117. The method of claim 86, whereby step (e) is independent of order of said mixing said first chemical entity of said pre-catalyst, with said second chemical entity of said co-catalyst, with the alpha-olefin monomer to be catalytically polymerized.

118. The method of claim 86, wherein conditions for performing step (a) through step (e) include a pressure range of from about 1 bar to about 30 bar and a temperature range of from about −78° C. to about 150° C., with exclusion of moisture and oxygen.

119. The method of claim 86, wherein conditions for performing step (a) through step (e) include a pressure range of from about 1 bar to about 5.5 bar and a temperature range of from about 20° C. to about 30° C., with exclusion of moisture and oxygen.

120. The method of claim 86, wherein step (f) includes adding to said living catalytic polymerization reaction at least one other type and quantity of a chemical reagent for improving the living catalytic polymerization of the alpha-olefin monomer.

121. The method of claim 86, wherein step (g), said terminating said living catalytic polymerization reaction is performed by involving means selected from the group consisting of means initially external to said living catalytic polymerization reaction, means internal to said living catalytic polymerization reaction, and, a combination thereof, said external means is selected from the group consisting of adding an external quencher to said living catalytic polymerization reaction, removing remaining alpha-olefin monomer from said living catalytic polymerization reaction, and, a combination thereof, said internal means is selected from the group consisting of complete consumption of the alpha-olefin monomer, deactivation of said catalyst formed during said progression of said living catalytic polymerization reaction, and, a combination thereof.

122. The method of claim 86, whereby said living catalytic polymerization reaction is formed and progresses in a type of chemical reactor selected from the group consisting of a continuous flow chemical reactor, a batch chemical reactor, and, a plug-flow chemical reactor, where size of said chemical reactor is selected from the group consisting of a micro-scale laboratory chemical reactor, a product/process development scale chemical reactor, and a large scale commercial chemical reactor.

123. The method of claim 86, whereby said living catalytic polymerization reaction is a type of chemical process selected from the group consisting of a continuous flow chemical process, a batch chemical process, and, a plug-flow chemical process, said chemical process is of a size selected from the group consisting of a micro-scale laboratory chemical process, a product/process development scale chemical process, and, a large scale commercial chemical process.

124. The method of claim 86, whereby said living catalytic polymerization reaction is formed and progresses in a temperature range of from about 25° C. to about 50° C.

125. The method of claim 86, whereby said living catalytic polymerization reaction is formed and progresses in a temperature range of from about 25° C. to about 50° C., whereby said catalyst formed during said living catalytic polymerization reaction remains living for a period of time of about 30 hours.

126. The method of claim 86, whereby said living catalytic polymerization reaction additionally features block co-polymerization of the alpha-olefin monomer.

127. The method of claim 86, whereby said living catalytic polymerization reaction is formed and progresses in a temperature range of from about 25° C. to about 50° C., and additionally features block co-polymerization of the alpha-olefin monomer in said temperature range.

128. The method of claim 86, whereby said at least one poly(alpha-olefin) product is produced having a molecular weight of about 450,000 grams/mole in a living fashion.

129. The method of claim 86, whereby said at least one poly(alpha-olefin) product is produced having a molecular weight of about 450,000 grams/mole in a living fashion with a polydispersity index (PDI) of about 1.1.

130. The method of claim 86, wherein the alpha-olefin monomer is selected from the group consisting of ethylene, propylene, 1-pentene, 1-hexene, 1-octene, 1,5-hexadiene, and, a higher alpha-olefin monomer.

* * * * *